(12) United States Patent
Kutty et al.

(10) Patent No.: US 9,814,573 B2
(45) Date of Patent: Nov. 14, 2017

(54) METHOD OF PREPARING A TISSUE SWATCH FOR A BIOPROSTHETIC DEVICE

(71) Applicant: St. Jude Medical, Cardiology Division, Inc., St. Paul, MN (US)

(72) Inventors: Jaishankar K. Kutty, Oakdale, MN (US); Aaron J. Chalekian, Savage, MN (US); Aditee A. Kurane, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 591 days.

(21) Appl. No.: 14/193,851

(22) Filed: Feb. 28, 2014

(65) Prior Publication Data
US 2014/0257472 A1    Sep. 11, 2014

Related U.S. Application Data

(60) Provisional application No. 61/775,173, filed on Mar. 8, 2013.

(51) Int. Cl.
| | |
|---|---|
| *A61L 31/14* | (2006.01) |
| *A61F 2/24* | (2006.01) |
| *A61L 27/36* | (2006.01) |

(52) U.S. Cl.
CPC ........ *A61F 2/2415* (2013.01); *A61L 27/3604* (2013.01); *A61L 27/3625* (2013.01); *A61L 27/3683* (2013.01); *A61F 2250/0036* (2013.01)

(58) Field of Classification Search
CPC ........... A61F 2/2415; A61F 2250/0036; A61L 27/3604; A61L 27/3683; A61L 27/3625
See application file for complete search history.

(56) References Cited

U.S. PATENT DOCUMENTS

| | | | |
|---|---|---|---|
| 5,613,982 A | 3/1997 | Goldstein | |
| 5,836,313 A * | 11/1998 | Perez | A61L 27/52 |
| | | | 128/898 |
| 5,842,387 A * | 12/1998 | Marcus | B23P 15/40 |
| | | | 76/104.1 |
| 6,682,559 B2 | 1/2004 | Myers et al. | |
| 6,872,226 B2 | 3/2005 | Cali et al. | |
| 7,141,064 B2 | 11/2006 | Scott et al. | |
| 7,189,259 B2 | 3/2007 | Simionescu et al. | |
| 7,594,974 B2 | 9/2009 | Cali et al. | |
| 8,043,450 B2 | 10/2011 | Cali et al. | |
| 2002/0091441 A1 * | 7/2002 | Guzik | A61F 2/2415 |
| | | | 623/2.13 |
| 2005/0165480 A1 | 7/2005 | Jordan et al. | |
| 2011/0238167 A1 | 9/2011 | Dove et al. | |

(Continued)

OTHER PUBLICATIONS

International Search Report and Written Opinion for Application No. PCT/US2014/019403 dated Apr. 23, 2014.

(Continued)

*Primary Examiner* — Christine H Matthews
*Assistant Examiner* — Joshua D Lannu
(74) *Attorney, Agent, or Firm* — Lerner, David, Littenberg, Krumholz & Mentlik, LLP

(57) ABSTRACT

A method of preparing a tissue swatch comprising one or more desired thicknesses for use in the manufacture of a bioprosthetic device, said method comprising sectioning a sheet of frozen tissue to produce a tissue swatch of said one or more desired thicknesses.

23 Claims, 12 Drawing Sheets

(56) References Cited

U.S. PATENT DOCUMENTS

2012/0208184 A1* 8/2012 Ragan ................ G01N 1/06
435/6.11
2013/0012767 A1 1/2013 Nguyen et al.

OTHER PUBLICATIONS

Connolly et al., Triglycidylamine Crosslinking of Porcine Aortic Valve Cusps or Bovine Pericardium Results in Improved Biocompatibility, BioMechanics and Calcification Resistance, American Journal of Pathology, vol. 166, No. 1, Jan. 2005 Copyright American Society for Investigative Pathology.
Okamoto Kiyoshi, Refrigeration, 2006, 81:949, pp. 913-918 (English abstract only).
Okamoto Kiyoshi et al., Estimation of Temperature Range for Cryo Cutting of Frozen Mackerel using DSC, Transactions of the Japan Society of Refrigeration and Air Conditioning Engineers, vol. 23 (2006) 23, No. 2, pp. 105-111. (English abstract only).
Okamoto Kiyoshi et al., The Effect of Muscle Fiber Direction on the Cut Surface Angle of Frozen Fish Muscular Tissue Cut by Bending Force, Nippon Shokuuhin Kagaku Kaishi, vol. 43, No. 9, 1035-1041; 1996.

* cited by examiner

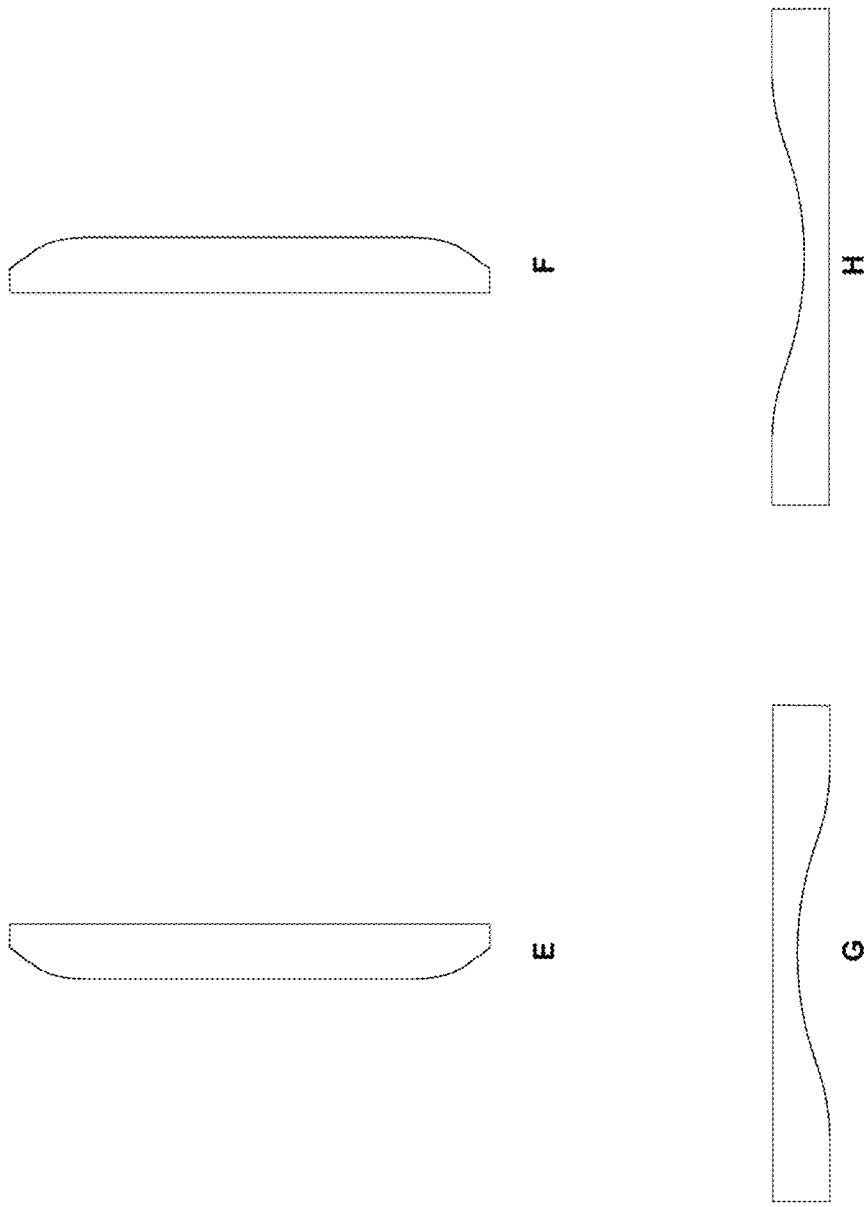

METHOD OF PREPARING A TISSUE SWATCH FOR A BIOPROSTHETIC DEVICE

CROSS-REFERENCE TO RELATED APPLICATIONS

The present application claims the benefit of the filing date of U.S. Provisional Patent Application No. 61/775,173 filed Mar. 8, 2013, the disclosure of which is hereby incorporated herein by reference.

BACKGROUND OF THE INVENTION

Prosthetic devices for clinical application are well known. Prosthetic devices which comprise biomaterials, e.g., mammalian tissue of human cadaver or non-human origin, are commonly referred to as "bioprosthetics". Bioprosthetic devices are frequently used in interventional cardiology, and typically comprise pericardial tissue of human, equine, porcine, ovine, and particularly, bovine origin. Incorporated therein, this exogenous tissue can perform a variety of functions, e.g., as a sewing rim or cuff on a harvested tissue heart valve. Pericardial tissue may also serve as valve leaflets in combination with the structural components of a bioprosthetic heart valve. Several commercially available bioprosthetic devices of this sort which provide excellent hemodynamic performance include, e.g., the TRIFECTA, BIOCOR, and EPIC stented valves and valve systems available from St. Jude Medical, Inc. (St. Paul, Minn.).

While pericardial tissue may be of sufficient tensile strength and durability for use in implantable cardiovascular devices, current methods for harvesting and processing such tissue are limited. Such processing methods include compression based techniques to reduce tissue thickness, e.g., such as described in U.S. Pat. No. 7,141,064. The use of lasers and other mechanical devices to reduce the overall tissue thickness are also described in U.S. 2011/0238167.

Notwithstanding, there remains a need for improved methods for preparing tissue swatches for use in the manufacture of bioprosthetic devices. Specifically, methods which are capable of consistently and efficiently producing tissue swatches of uniform thickness, including uniformly very thin sections of pericardial tissue, as well as tissue swatches of varying thicknesses by design for configuration and incorporation in bioprosthetic cardiovascular devices, are needed.

BRIEF SUMMARY OF THE INVENTION

In a first aspect, the present invention relates to a method of preparing a tissue swatch comprising one or more desired thicknesses for use in the manufacture of a bioprosthetic device, said method comprising sectioning a sheet of frozen tissue to produce a tissue swatch of said one or more desired thicknesses. In a particular embodiment, the sectioning is performed using an apparatus suitable for controlled trimming of tissue from said sheet of frozen tissue. In a further embodiment, the apparatus is any high precision tissue slicing apparatus. In a particular embodiment, the apparatus is selected from the group consisting of a microtome, vibratome and a cryotome. In a particular embodiment, the apparatus is a cryotome.

In another aspect, the invention relates to a method of manufacturing a bioprosthetic device comprising sectioning a sheet of frozen tissue to produce a tissue swatch of one or more desired thicknesses; configuring said tissue swatch into a shape suitable for use in said bioprosthetic device; and incorporating said tissue swatch into said bioprosthetic device.

In a further aspect, the invention relates to a method of preparing a tissue swatch for use in the manufacture of a bioprosthetic device, said method comprising sectioning a tissue sheet suitable for use in the manufacture of a bioprosthetic device on a cryocutting apparatus, wherein said apparatus has been adjusted to produce a tissue swatch comprising one or more desired thicknesses.

In another aspect, the invention relates to a method of manufacturing a bioprosthetic device comprising
  a. sectioning a tissue sheet suitable for use in the manufacture of a bioprosthetic device on a cryocutting apparatus, wherein said apparatus has been adjusted to produce a tissue swatch comprising one or more desired thicknesses;
  b. configuring said tissue swatch into a shape suitable for use in said bioprosthetic device; and
  c. incorporating said tissue swatch into said bioprosthetic device.

In various embodiments of the above methods, the apparatus is adjusted to employ a straight or contoured blade to produce a tissue swatch of a desired uniform or varied thickness. In a particular embodiment, the apparatus is adjusted to employ a straight blade to produce a tissue swatch comprising a desired uniform or varied thickness.

In other embodiments of the methods, the apparatus is adjusted to employ a contoured blade to produce a tissue swatch of desired varied thickness. In a particular embodiment, the contoured blade is a convex blade and said tissue swatch is of concave thickness. In another particular embodiment, the contoured blade is a concave blade and said tissue swatch is of convex thickness.

In another embodiment of the above methods, the apparatus is adjusted to employ a flat or contoured specimen disk to produce a tissue swatch of uniform or varied thickness.

In additional aspects, the invention includes the tissue swatch comprising one or more desired thicknesses produced according to the methods of the present invention. In various embodiments, said tissue swatch comprises one or more thicknesses between about 0.001 to about 0.050 inches, more particularly between about 0.006 to about 0.043 inches, between about 0.010 to about 0.014 inches and between about 0.011 to about 0.013 inches. In a particular embodiment, the tissue swatch comprises a uniform thickness of about 0.012±0.001 inches. In one embodiment, the tissue swatch is of a concave thickness comprising thicker peripheral regions and a thinner inner central region. In a particular embodiment, the concave tissue swatch comprises thicker peripheral regions of about 0.014 inches thick, and a thinner inner central region of about 0.010 inches thick.

In another embodiment, the tissue swatch is of a convex thickness, thus comprising a thicker inner, central region and thinner peripheral regions. In a particular embodiment, the convex tissue swatch comprises thinner peripheral regions of about 0.010 inches thick, and a thicker inner central region of about 0.014 inches thick.

In further embodiments of the methods of the present invention, the tissue sheet is pericardial tissue. In various embodiments, the pericardial tissue is selected from the group consisting of pericardial tissue of human, bovine, equine, ovine and porcine origin. In a particular embodiment the pericardial tissue is of bovine origin.

In contemplated embodiments, the bioprosthetic device of the methods of the present invention is a bioprosthetic cardiovascular device. In a particular embodiment, the bioprosthetic cardiovascular device is selected from the group consisting of artificial heart valves, pericardial patches, vascular grafts or conduits, permanently in-dwelling percutaneous devices, vascular shunts, dermal grafts for wound healing, and surgical patches. In a particular embodiment, the bioprosthetic cardiovascular device is a bioprosthetic heart valve.

In a further aspect, the method of preparing a tissue swatch for use in the manufacture of a bioprosthetic device further comprises configuring the tissue swatch for incorporation in said bioprosthetic device, and optionally incorporating said configured tissue into the bioprosthetic device.

In various further embodiments of the methods of the present invention, the tissue swatch is configured for use as a sewing rim, cuff, or leaflet in a bioprosthetic device. In a particular embodiment, the tissue swatch is configured for use as a valve leaflet in a bioprosthetic heart valve. In a further particular embodiment, the tissue sheet is bovine pericardial tissue, and the tissue swatch is configured for use as a valve leaflet in a bioprosthetic heart valve.

In a further particular embodiment, the tissue swatch is configured for use in the bioprosthetic device such that one or more regions of greater thickness in said tissue swatch are incorporated in the bioprosthetic device in areas subjected to high stress in vivo.

In additional aspects the invention relates to the tissue swatch produced, as well as to the bioprosthetic device manufactured according to the methods of the present invention.

In yet another aspect, the invention relates to the use of the tissue swatch produced according to the methods of the present invention in the manufacture of a bioprosthetic device.

BRIEF DESCRIPTION OF THE DRAWINGS

FIG. 3(A) depicts a straight blade suitable for a cutting apparatus and a sectioned tissue swatch having a uniform desired thickness which may be produced with such blade. FIG. 3(B) depicts a blade with a convex curvature suitable for a cutting apparatus which can be used to produce a concave-shaped tissue swatch. FIG. 3(C) depicts a blade with a concave curvature suitable for a cutting apparatus which can be used to produce a convex-shaped tissue swatch.

FIGS. 4A, 4B, 4E-4H depict various isometric side views of the blade, while FIG. 4C is a back view, and FIG. 4D is a front view of the blade.

FIGS. 5A, 5B, 5E-5H depict various isometric side views of the swatch, while FIG. 5C is a back view, and FIG. 5D is a front view of the swatch.

FIG. 10A: thin spots; FIG. 10B: dry tissue (details circled); FIG. 10C: swatch tear; FIG. 10D: "chatter marks" (circled); and FIG. 10E: blade "witness marks" (circled).

DETAILED DESCRIPTION

Figure 1:
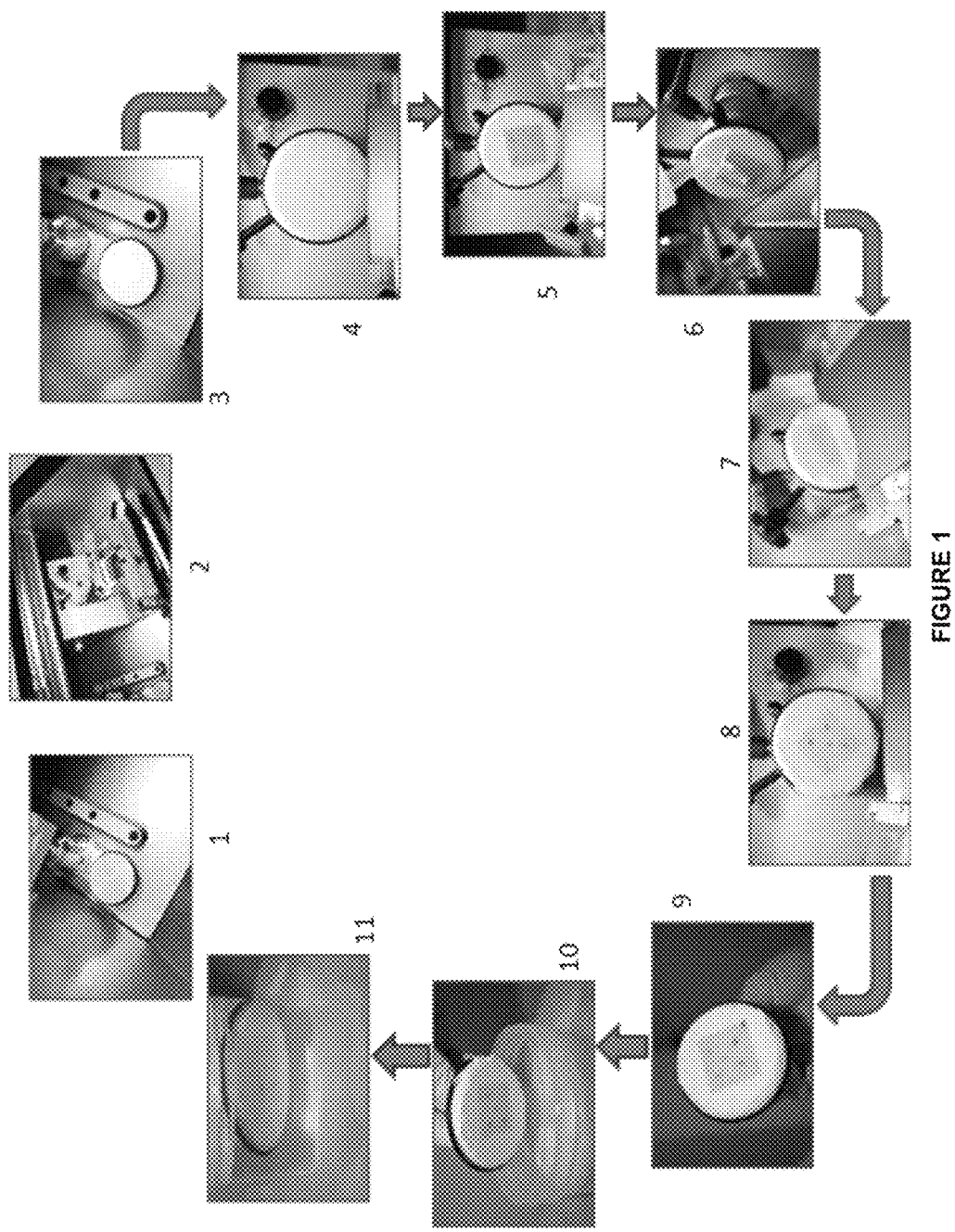
FIG. 1 depicts steps involved in sectioning a tissue sheet on a cryocutting apparatus comprising the use of embedding gel according to a contemplated embodiment of the methods of the present invention. Images 1-4 depict several steps associated with adjusting a cryocutting apparatus familiar to one of skill in the art, including: (1) introducing the specimen disk into the cryocutting apparatus for temperature equilibration; (2) mounting a blade into the cryocutting apparatus; (3) introducing an embedding medium onto the specimen disk of the cryocutting apparatus (e.g., in order to prepare a flat or contoured reference surface) for tissue mounting, and (4) introducing the specimen disk comprising the embedding medium into the cryocutting apparatus. Image 5 depicts a tissue sheet of bovine pericardial tissue placed on top of embedding medium which has been applied to the specimen disk, and image 6 depicts covering the tissue sheet with additional embedding medium. Images 7-8 depict the sectioning of the tissue sheet to produce a tissue swatch of a desired thickness. Image 9 depicts dismounting the cryocut tissue swatch from the specimen disk and images 10-11 depict immersing the tissue swatch into room temperature saline to thaw the tissue swatch.

While the specification concludes with the claims particularly pointing and distinctly claiming the invention, it is believed that the present invention will be better understood from the following description.

All percentages and ratios used herein are by weight of the total composition unless otherwise indicated herein. All measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Unless otherwise indicated, as used herein, "a" and "an" include the plural, such that, e.g., "a bioprosthetic device" can mean at least one bioprosthetic device, as well as a plurality of bioprosthetic devices, i.e., more than one bioprosthetic device, including but not limited to, bioprosthetic devices of different types.

Where used herein, the term "and/or" when used in a list of two or more items means that any one of the listed characteristics can be present, or any combination of two or more of the listed characteristics can be present. For example, if a tissue sheet or tissue swatch is described as containing characteristics A, B, and/or C, the tissue sheet or tissue swatch can contain A feature alone; B alone; C alone; A and B in combination; A and C in combination; B and C in combination; or A, B, and C in combination.

The present invention relates to methods for preparing tissue swatches for use in the manufacture of a bioprosthetic device, as well as methods of manufacturing a bioprosthetic device, and tissue swatches and bioprosthetic devices produced according to said methods.

As contemplated herein, the methods of the present invention can be used to produce a tissue swatch comprising one or more desired thicknesses for use in the manufacture of a bioprosthetic device. Specifically, as described herein in detail, tissue swatches having a consistent uniform thickness which meet a desired technical specification range for various bioprosthetic devices are now possible according to the methods of the present invention. In addition, said method may also be used to produce tissue swatches which comprise one or more areas which are thicker in comparison to other areas of the tissue swatch by design, depending on the intended use of the tissue swatch in a bioprosthetic device. Thus, as used herein, "a tissue swatch comprising one or more desired thicknesses" includes not only a tissue swatch of a uniform thickness but also a "tissue swatch of varied thickness", i.e., a tissue swatch which comprises one or more desired elevations and depressions in the tissue swatch.

As contemplated herein, the methods of the present invention to produce a tissue swatch comprising one or more desired thicknesses comprise sectioning a sheet of frozen tissue. As understood herein, the use of frozen tissue in the methods of the present invention provides several advantages as it not only minimizes shear-associated damage to the tissue, but also facilitates holding the tissue swatch in place in the cutting apparatus during sectioning. As contemplated herein, any method for freezing and sectioning a tissue sheet may be used in the instant methods as long as it does not negatively impact the intended use of the sectioned tissue swatch in a bioprosthetic device. In this regard, as understood by one of skill in the art, it is contemplated herein that ideally the length of time that the tissue is frozen should be kept to a minimum to avoid any possible damage to the tissue; for example, not to exceed 20 minutes. Also, best results are obtained by setting the machine such that the chamber temperature (or temperature of the freezer, cold room, or other work area in which a microtome or vibratome, etc. is used), does not fall below −20° C. and not more than 8 microns of the tissue is removed with every slice.

As contemplated herein, "freezing" tissue refers to subjecting a tissue sheet to a temperature of approximately −5° C. to −20° C., e.g., such that the tissue sheet is capable of being held in position on the apparatus to facilitate the cutting process. Thus, a "frozen tissue sheet" is a tissue sheet subjected to such reduced temperatures. It is understood herein that tissue can be frozen and sectioned according to the methods of the present invention without negatively impacting the physical properties of the tissue or intended use in a bioprosthetic. Ideally, as discussed above, the methods of the present invention should be performed in a manner such that the tissue sheet is not frozen for an extended period of time, e.g., ideally no longer than approximately 20 minutes. Also, best results are obtained by setting the machine such the chamber temperature (or temperature of the freezer, cold room, or other work area in which a microtome or vibratome, etc. is used), does not fall below −20° C. and not more than 8 microns of the tissue is removed with every slice.

Any apparatus which permits carefully controlled trimming of tissue from a frozen tissue sheet may be used in the methods of the present invention. Such cutting apparatus are familiar to one of skill in the art and include, but are not limited to, cryotomes. In addition, also contemplated herein are other high precision tissue slicing apparatuses such as vibratomes, and microtomes. Indeed, while typically not used for sectioning frozen tissue, it is contemplated herein that conventional microtomes and vibratomes may be used with the methods of the instant invention as long as the device and the tissue sheet to be sectioned is kept sufficiently cold; this may be easily achieved by using these machines in a walk-in freezer or other cold room at a temperature sufficient to ensure that the tissue sheet on the cutting apparatus remains frozen during sectioning. Alternatively, the device may be used in a freezer chest or other container the temperature of which may be maintained to permit the sectioning of frozen tissue.

Similarly, non-mechanized devices for cutting frozen tissue are also contemplated herein. Thus, for example, any blade mechanism in combination with a tissue retention mechanism that can be used together to cut frozen tissue may be used. Specifically, as with a microtome or vibratome, such combination of blade mechanism and tissue retention mechanism may be used in a freezer to ensure that the tissue sheet remains frozen during sectioning.

In a particular embodiment, it is contemplated herein that the present invention relates to a method of preparing a tissue swatch for use in the manufacture of a bioprosthetic device, said method comprising sectioning a tissue sheet suitable for use in the manufacture of a bioprosthetic device on a cryocutting apparatus, wherein said apparatus has been adjusted to produce a tissue swatch of one or more desired thicknesses.

As envisioned herein, in various embodiments, the methods of the present invention can employ a cryotome which can be adjusted to employ straight or contoured blades, and/or a specimen disk with a flat or contoured surface.

It is understood herein that the various blades and specimen disks described herein can be used in the methods of the present invention in any combination and thus achieve a tissue swatch of any one or more desired thicknesses. For example, and without any intended limitation, a straight blade and a specimen disk with a flat surface can be used together to create a tissue swatch of a desired uniform thickness. Alternatively, a cutting apparatus such as a cryotome can be adjusted to employ a contoured blade and a specimen disk with a flat surface, or adjusted to employ a contoured or straight blade and a specimen disk with a contoured surface, to produce a tissue swatch comprising one or more desired thicknesses. Accordingly, a tissue swatch comprising one or more elevations and depressions in the tissue swatch can be produced.

As contemplated herein, a tissue swatch of any one or more desired thicknesses can be produced according to the methods of the present invention. As appreciated by one of skill in the art, the exact dimensions of a tissue swatch produced according to the methods of the present invention can be designed as desired given the intended use of the tissue swatch in the bioprosthetic device in which the tissue swatch is to be incorporated. Thus, as used herein, a "desired" thickness refers to the thickness of a tissue swatch that is suitable for use in the particular bioprosthetic device for which the tissue swatch is intended.

Suitable tissue swatch thicknesses for bioprosthetic devices are familiar to one of skill in the art, and as discussed above, can vary depending upon the intended use of the device, as well as the source of the tissue. Generally, such tissue swatches can suitably range from about 0.001 to about 0.050 inches, however, such range is only intended as an example herein, and without intending to limit the scope of the instant invention.

As understood herein, a tissue swatch can be of one thickness, i.e., of uniform thickness, or can be of more than one thickness and thus comprise one or more desired elevations and depressions, and thus be of "varied thickness". In particular embodiments contemplated herein, tissue swatches produced according to the methods of the instant invention can be designed to comprise one or more regions of greater thickness (and thus enhanced durability) which can be strategically employed in a bioprosthetic device in areas subject to high stress in vivo.

As used herein, the term "high stress" with regard to the use and function of bioprosthetic devices in vivo is understood by one of skill in the art, and refers, e.g., to the increased load on a bioprosthetic device in vivo, such as that placed on a heart valve leaflet when the valve is in the closed position. Thus, in the case of a heart valve leaflet, a tissue swatch of varied thickness can be configured for use as a valve leaflet and strategically incorporated in a bioprosthetic heart valve such that thicker areas of the leaflet are placed at commissural attachments (the highest point of leaflet attachment to the stent) where the leaflet is subjected to maximum stress.

As used herein, a "tissue swatch of consistently uniform desired thickness" and like terms are understood by one of skill in the art as being virtually free of regions that are too thick or too thin for the intended purpose of the tissue swatch. It a contemplated embodiment, such tissue swatch can comprise approximately the same desired thickness throughout the tissue swatch, +/−0.001 inch.

As understood by one of skill in the art, as used herein, the terms "thick", "thin", "very thin", "thicker", "thinner" and the like, are relative terms. Thus, the actual dimensions in inches of a thickness that is deemed "thick", "thin", "very thin", etc. can vary depending on the bioprosthetic device. Accordingly, reference herein to a tissue swatch comprising a "varied thickness" or which comprises "one or more desired thicknesses" or "one or more desired elevations and depressions" is understood by one of skill in the art as referring to a tissue swatch produced according to the methods of the present invention which can be designed to have one or more regions that are thicker than one or more other regions in the same tissue swatch, yet on the whole, the swatch is of a sufficient overall thickness for its intended use in a bioprosthetic device.

As contemplated herein, the tissue swatches produced according to the methods of the present invention are particularly suitable for the manufacture of a bioprosthetic device for cardiovascular applications. For example, by reducing the presence of regions that are too thick, tissue swatches made according to the methods of the present invention can be reliably used to manufacture bioprosthetic devices with uniformly lower crimp profiles, thus producing a device which is less invasive. Similarly, since excessively thin regions compromise the integrity of a tissue swatch, the tissue swatches of the present invention can be used to create bioprosthetic devices with enhanced durability.

Generally, for cardiovascular applications, suitable thicknesses for a tissue swatch can range from between about 0.001 to about 0.050 inches. In various embodiments, the tissue swatch can have one or more regions in thickness between about 0.001 to about 0.050 inches, between about 0.006 to about 0.043 inches, between about 0.010 to about 0.014 inches, and between about 0.011 to about 0.013 inches. In a particular embodiment, the tissue swatch comprises a uniform thickness with a targeted nominal value of about 0.012±0.001 inches. As understood by one of skill in the art, a "targeted nominal value" refers to the average thickness value of the tissue swatch. Such tissue swatch can be used in a valve leaflet, e.g., in present generation heart valve leaflet applications.

As contemplated herein, a tissue swatch produced according to the present methods can be referred to herein as being "very thin". As understood by one of skill in the art of bioprosthetic devices, and particularly in the field of cardiovascular devices, such tissue swatch can comprise one or more regions between about 0.005 inches to about 0.012 inches, and can be used to facilitate the manufacture of minimally invasive bioprosthetic devices.

As used herein, a "tissue swatch comprising one or more desired elevations and depressions in the tissue swatch" refers to tissue swatches of varied thickness, i.e., comprising one or more regions of different thickness. Such tissue swatches include but are not limited to tissue swatches comprising a convex or concave thickness produced using the blades and/or specimen disks as disclosed herein.

Figure 3:
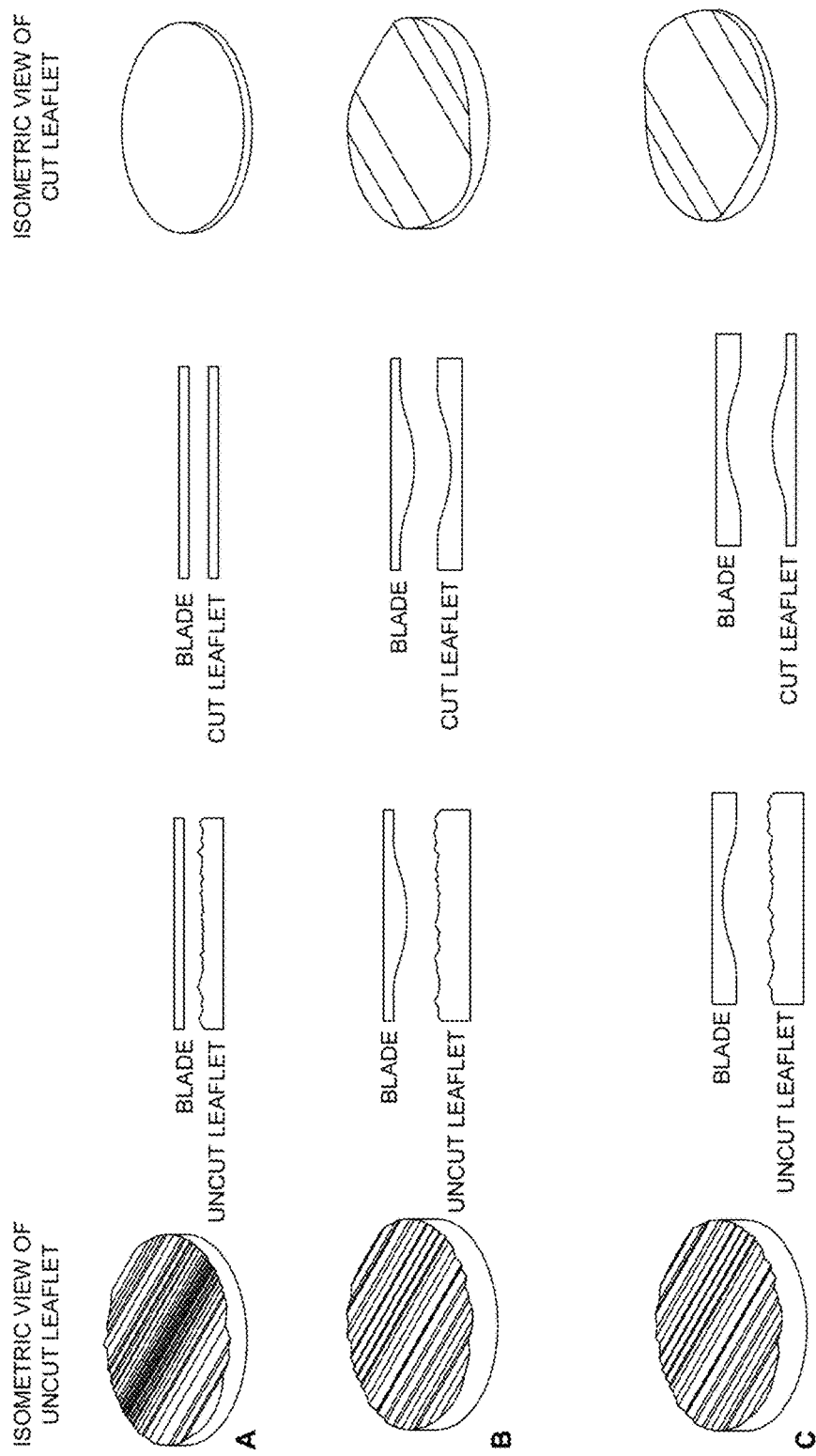
FIG. 3 depicts various blade conformations contemplated for use with the methods of the present invention, as well as isometric views of sectioned tissue swatches ("cut leaflets"). As provided therein.
Figure 4:
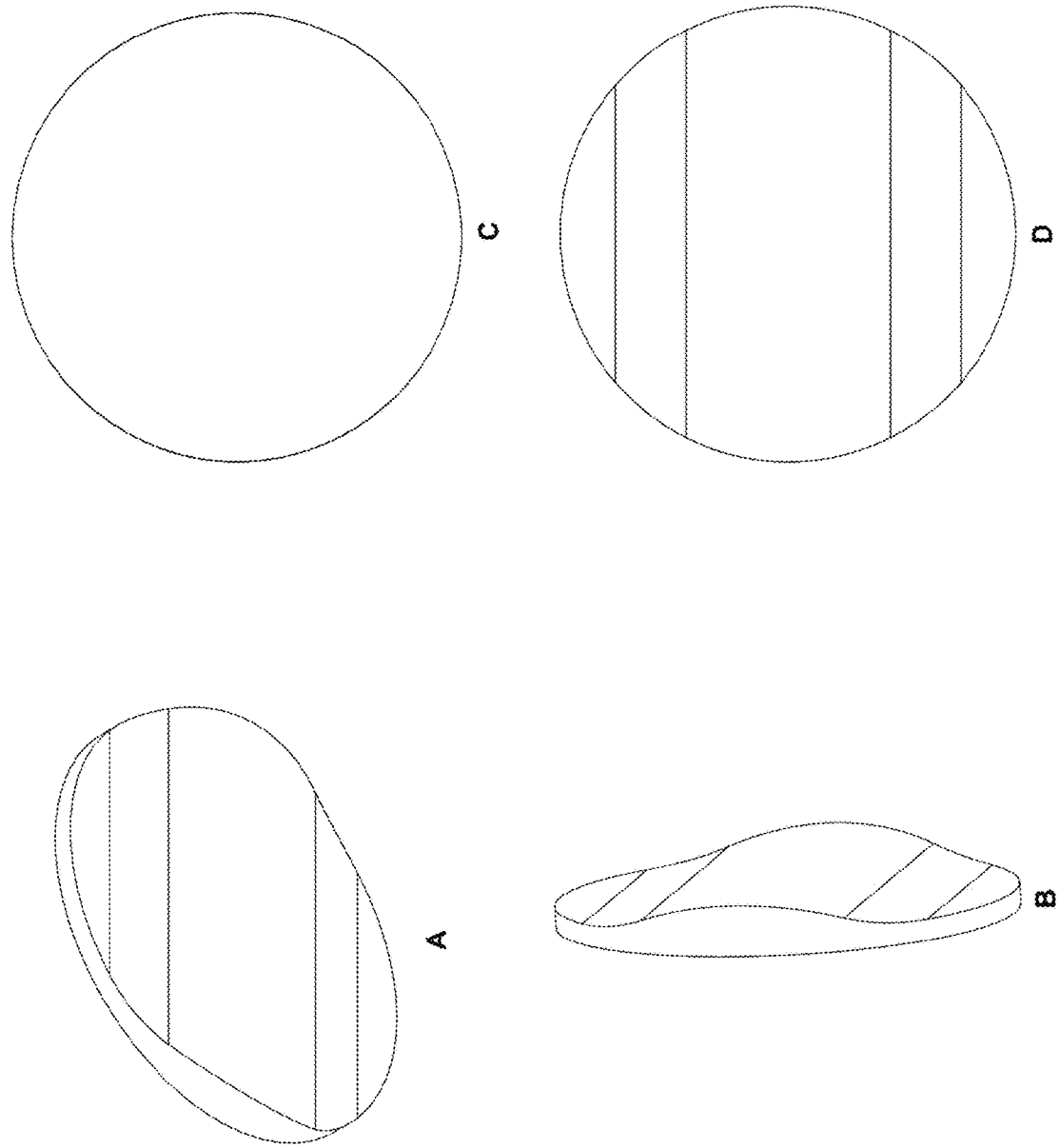
FIG. 4 depicts a convex contoured blade contemplated for use with the methods of the present invention to produce a tissue swatch of varying thickness.
Figure 4:
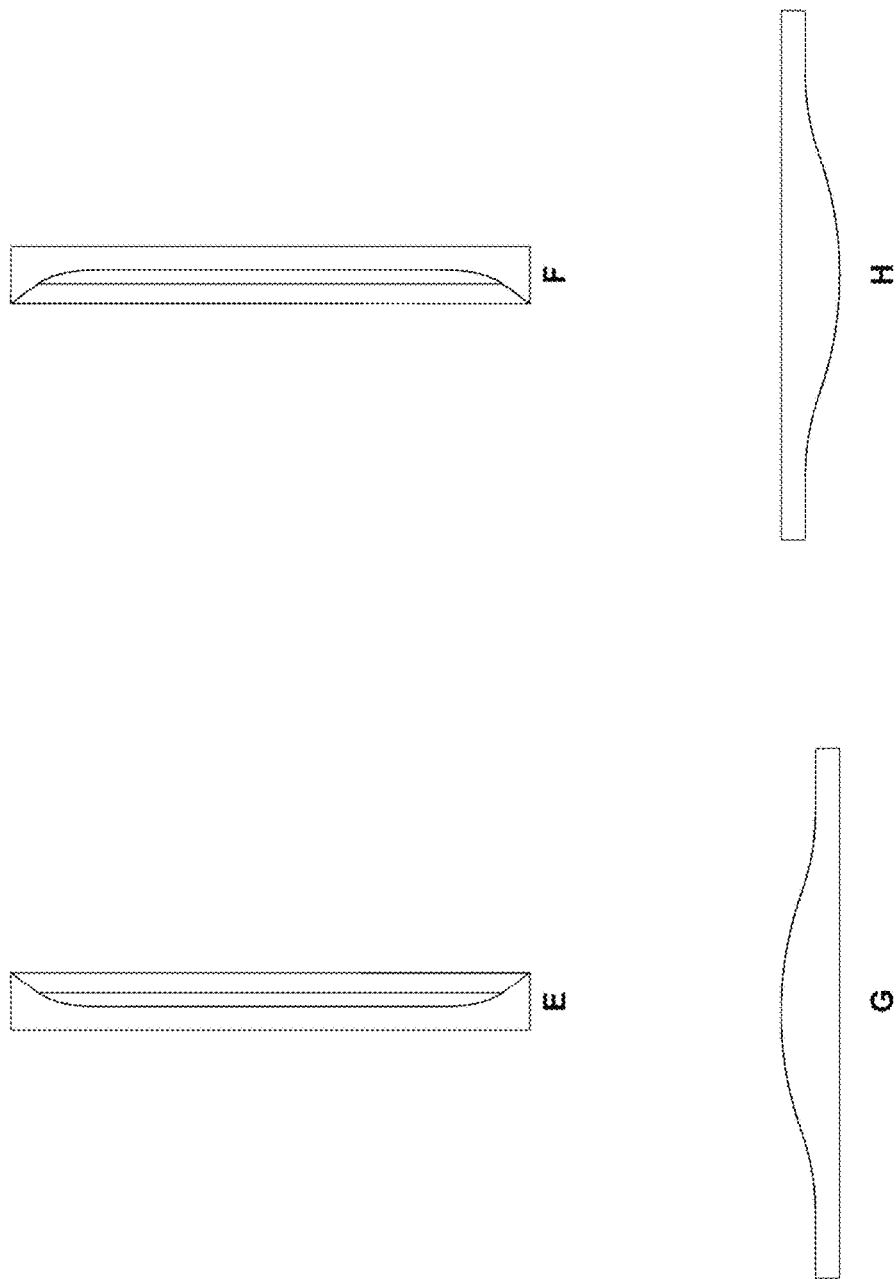
Figure 5:
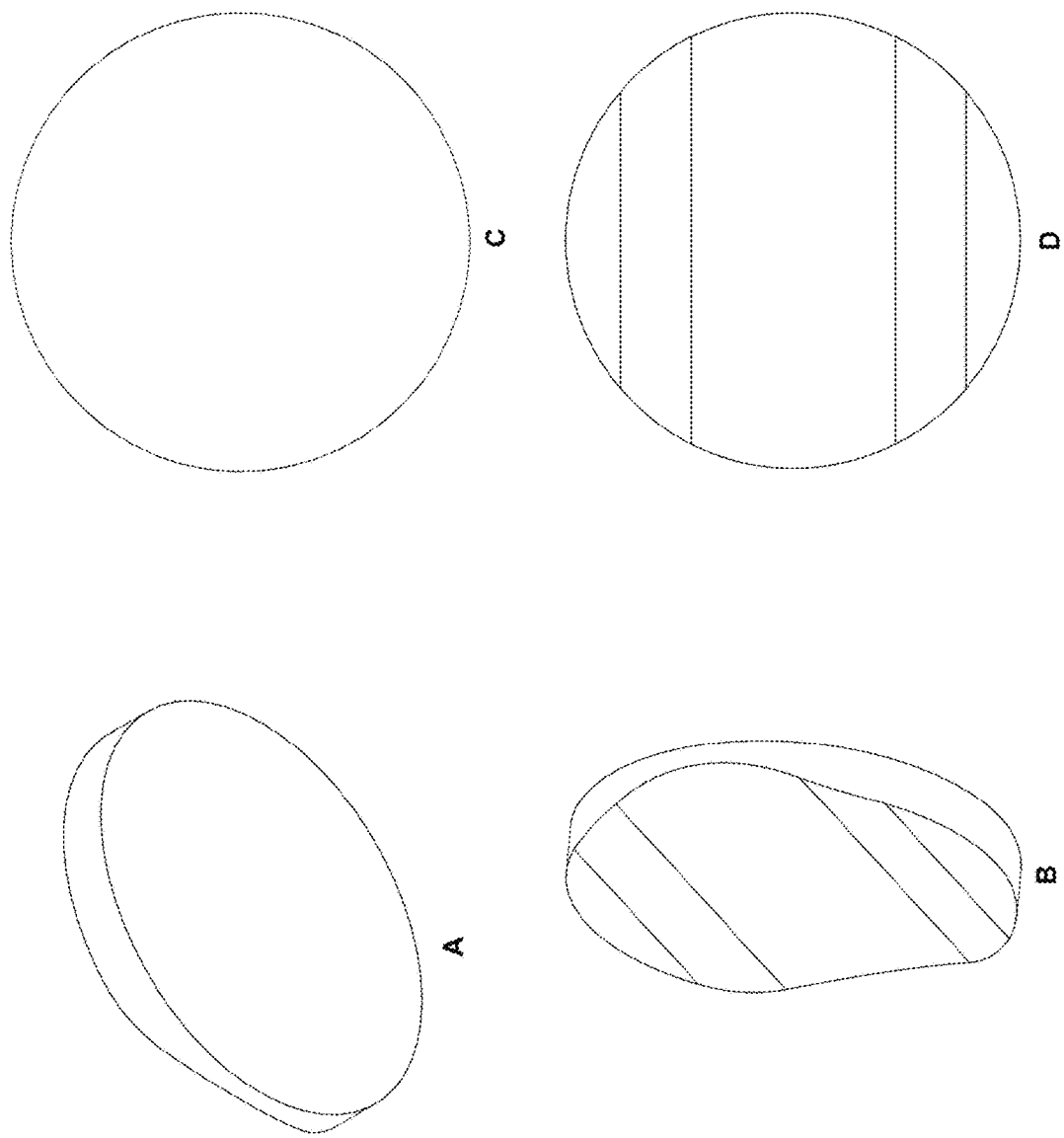
FIG. 5 depicts a concave contoured tissue swatch, e.g., produced using a convex contoured blade such as depicted in FIG. 4.
Figure 6:
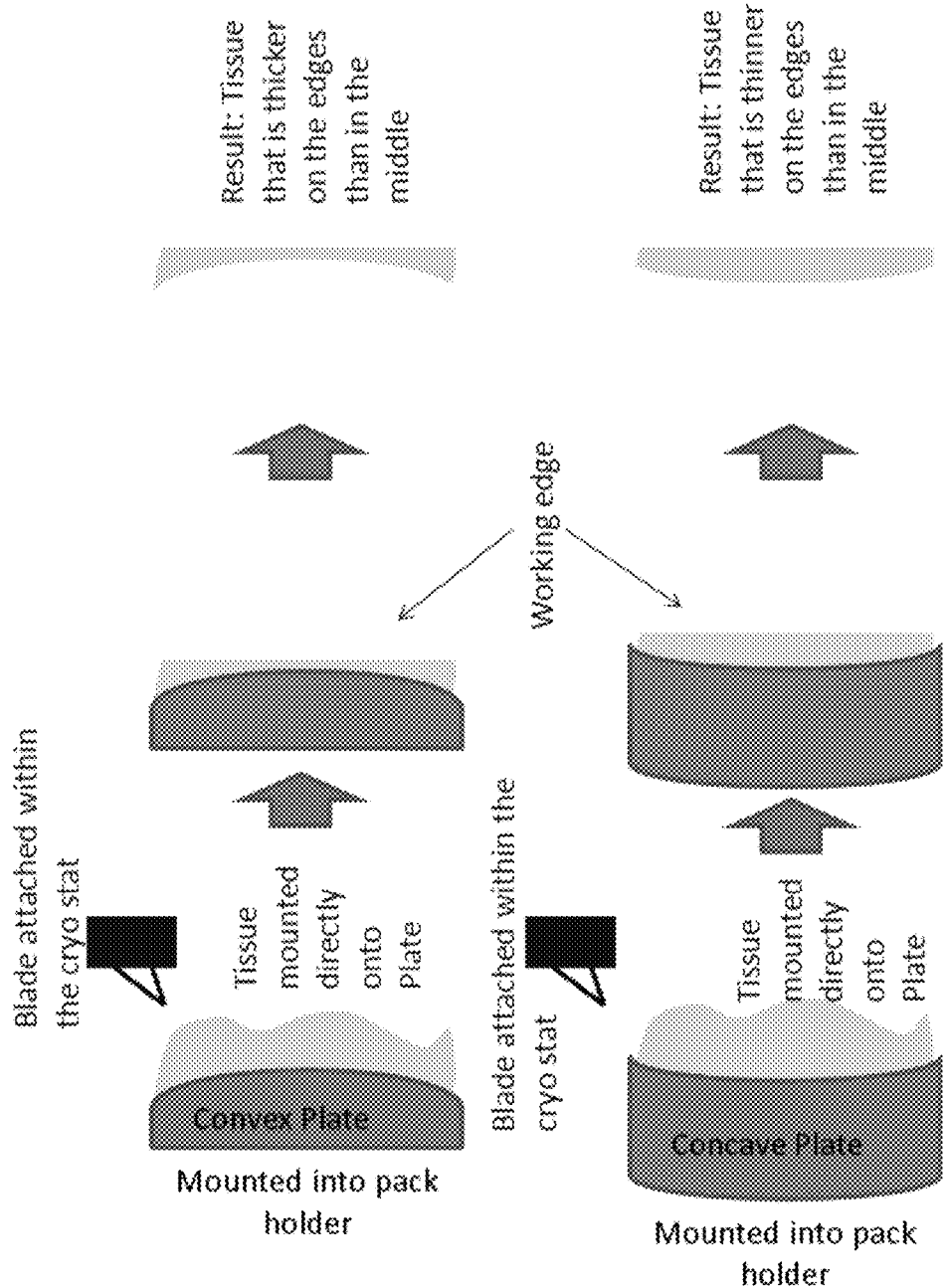
FIG. 6 depicts the use of convex and concave shaped mounting plates that may be used with the methods of the present invention to produce a sectioned tissue swatch with a concave shape (tissue swatch thicker on the edges than in the middle) or convex shape (tissue swatch thinner on the edges than in the middle), respectively, when sectioned with a straight blade. While embedding gel may be used with these plates, the figure depicts the mounting plates without the use of embedding gel.
Figure 7:
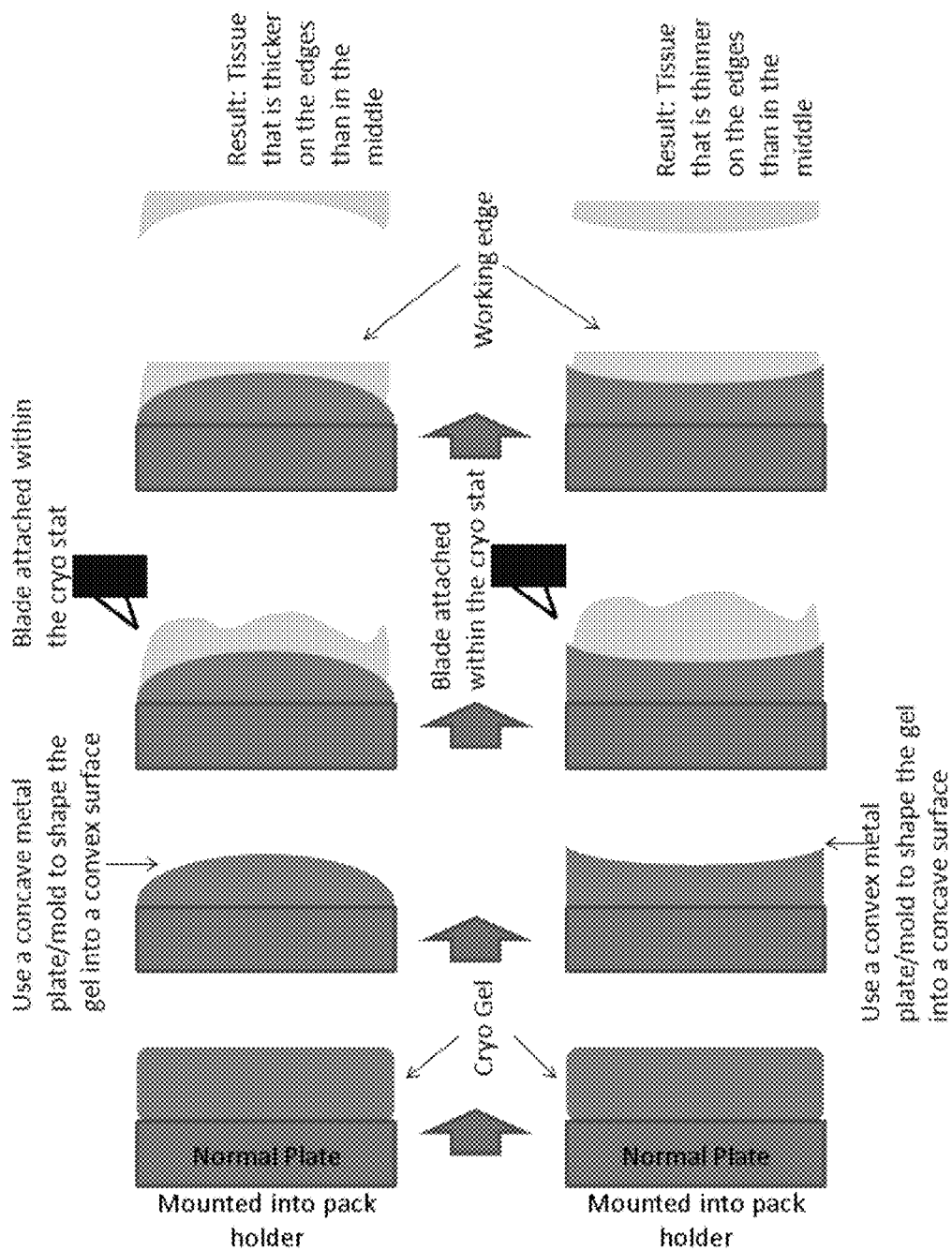
FIG. 7 depicts the use of flat mounting plates with cryogel molded to have a convex or concave shaped surface, and which can be used to produce a tissue swatch with a concave shape (tissue swatch thicker on the edges than in the middle) or convex shape (tissue swatch thinner on the edges than in the middle), respectively, when sectioned with a straight blade.
Figure 8:
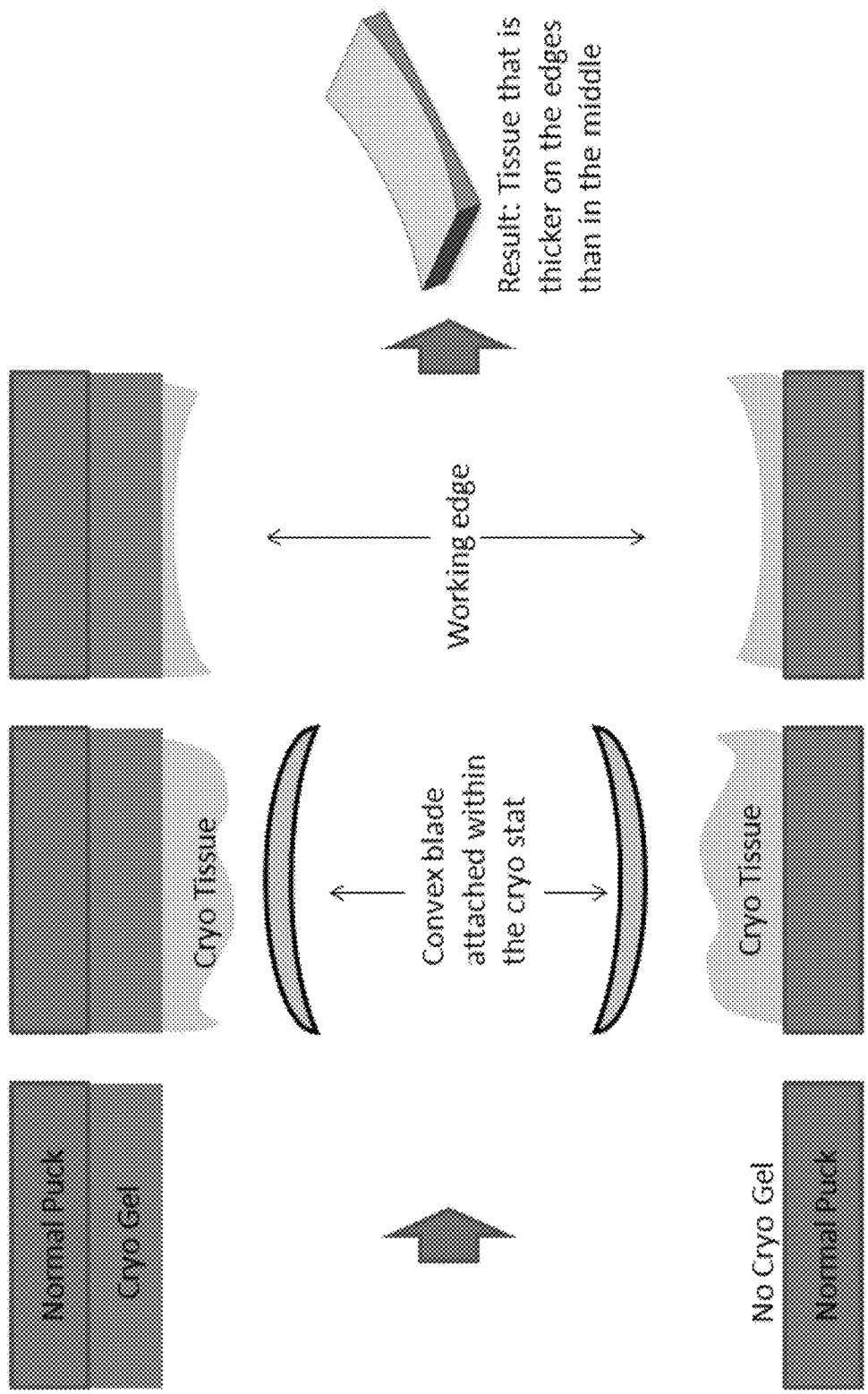
FIG. 8 depicts sectioning tissue using a flat mounting plate ("normal puck") with or without embedding gel ("cryogel") and using a cryotome with a convex blade. The resulting tissue swatch is thicker on the edges than in the middle.
Figure 9:
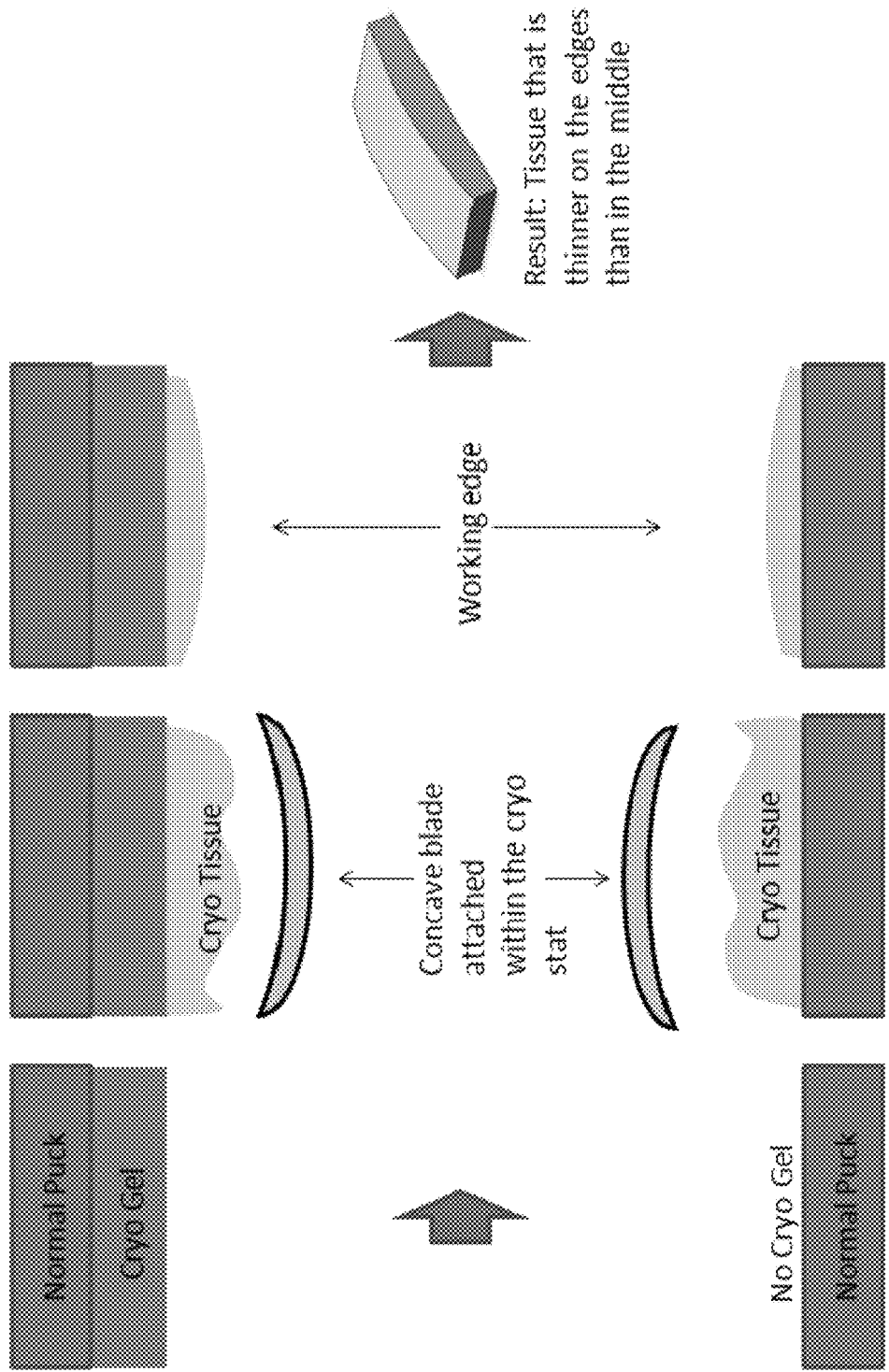
FIG. 9 depicts sectioning tissue using a flat mounting plate ("normal puck") with or without embedding gel ("cryogel") and using a cryotome with a concave blade. The resulting tissue swatch is thinner on the edges than in the middle.

As understood by one of skill in the art, a tissue swatch comprising a concave thickness comprises thicker peripheral regions and a thinner inner central region. In another embodiment, the tissue swatch is of a convex thickness, thus comprising an inner thicker central region and thinner peripheral regions. FIG. 3 provided herein is a schematic representation of possible tissue swatches of uniform, concave and convex thickness. For example, a tissue swatch of uniform desired thickness produced by a straight blade is depicted at FIG. 3(A). FIG. 3(B) depicts a tissue swatch of concave thickness comprising a central region of reduced thickness bordered by regions of greater thickness in comparison and produced using a blade with a convex contour. A tissue swatch with a convex thickness comprising an inner region of greater thickness bordered by outer regions of reduced thickness in comparison produced using a blade with a concave contour is depicted at FIG. 3(C).

As discussed above, for instance, for cardiovascular applications, the thickness of a tissue swatch can range between about 0.001 to about 0.050 inches. This is true with regard to tissues not only of uniform thickness but also of tissue swatches comprising desired regions of varying thickness. Accordingly, with regard to the latter, in various embodiments, a tissue section can have one or more desired elevations and depressions in thickness ranging between about 0.001 to about 0.050 inches, between about 0.006 to about 0.043 inches, between about 0.010 to about 0.014 inches and between about 0.011 to about 0.013 inches.

As particularly contemplated herein, a concave tissue swatch can comprise thicker peripheral regions of about 0.014 inches thick, and a thinner inner central region of about 0.010 inches thick. In another particular embodiment, a convex tissue swatch can comprise thinner peripheral regions of about 0.010 inches thick, and a thicker inner central region of about 0.014 inches thick.

FIGS. 3-9 provided in the instant application depict only a few examples of possible tissue swatches of uniform or varying thickness and blade contours contemplated herein, and is not intended to limit the scope of the present invention in any way. Indeed, in addition to tissue swatches with convex or concave thicknesses, tissue swatches with a variety of varying thicknesses could be produced according to the methods of the present invention depending on the particular contour of the blade used to section the tissue and/or the surface contour of the specimen disk. Thus, it is envisioned herein that tissue sheets can be sectioned according to the methods of the present invention such that the resulting tissue swatches comprise a variety of thicknesses depending on the intended use of the tissue swatch, e.g., depending on the type of bioprosthetic device in which the tissue swatch is to be incorporated.

As provided herein, the methods of the present invention include, or can optionally include, a step wherein the tissue swatch is further configured to reflect the intended function of tissue swatch in the bioprosthetic device in vivo. The invention also includes methods wherein, optionally, the configured tissue swatch is incorporated into the bioprosthetic device for which it was intended. Thus, for example, as envisioned herein, a tissue swatch can be produced which comprises one or more desired thicknesses, and which is then specifically configured for use as a heart valve leaflet and incorporated in a transcatheter aortic valve (TAVI).

Methods for configuring tissue swatches for use in bioprosthetic devices are familiar to one of skill in the art and can be used in conjunction with the methods of preparing tissue swatches disclosed herein. Thus, depending upon the intended use of the tissue swatch in a bioprosthetic device, the tissue swatch can be cut using conventional methods to produce a tissue swatch of appropriate shape and dimension, e.g., to make a valve leaflet or other component, which is then incorporated into a medical device.

Methods of manufacturing a bioprosthetic device, including methods of incorporating a configured tissue swatch into a bioprosthetic device, are also familiar to one of skill in the art. Such methods of manufacture typically include, e.g., suturing said configured tissue swatch into place in the device.

As particularly contemplated herein, methods of manufacture of a bioprosthetic device which employ the tissue swatches of the present invention can comprise a step wherein a tissue swatch of varied thickness is strategically incorporated into a bioprosthetic device such that regions of greater thickness are intentionally incorporated in the bioprosthetic device in areas where the device is subjected to high stress in vivo. In this regard, it is understood herein that one of skill in the art would be able to design and configure the necessary tissue swatch of varied thickness for such purpose.

As discussed herein, the production of very thin tissue swatches are possible according to the methods of the present invention. Thus, the present invention is particularly relevant given the desire for increasingly minimally invasive clinical procedures. Accordingly, as particularly envisioned herein, tissue swatches produced according to the methods of present invention are ideally suited for use in the manufacture of the next generation of cardiovascular medical devices. In particular, it is contemplated herein that the methods of the present invention can permit the manufacture of devices for delivery using delivery systems smaller than ever before, e.g., less than 18 French. Such tissue swatches can be used, e.g., as transcatheter heart valve leaflets and cuffs. Moreover, the methods disclosed herein permit the manufacture of a bioprosthetic device with reduced crimp profiles, e.g., from about 18 Fr or less, and particularly from about 16 Fr or less.

In addition to facilitating the production of bioprosthetic devices for the next-generation of minimally invasive procedures, the methods of the present invention also permit the manufacture of bioprostheses which possess enhanced durability and performance capabilities. For example, a tissue swatch comprising a varied thickness could be particularly useful in the creation of minimally invasive transcatheter heart valves by permitting the reduction in the overall mass of the valve, yet without compromising the function or durability of the valve. For example, a valve could comprise a tissue swatch of greater thickness only where necessary in the valve, e.g., in areas of high stress. Thus, such valve would be of sufficient durability for the intended use, but would improve ease-of-implantation since the reduction in the overall thickness of the tissue swatch would cause an overall reduction in the mass of the valve and thus produce reduced valve re-sheath forces during the valve replacement procedure. Accordingly, a tissue swatch of the present invention, and bioprosthetic devices made therewith, provide advantages not currently possible with tissue swatches produced according to conventional methods.

By permitting the creation of tissue swatches of uniform or varying thicknesses specifically designed for the intended use and delivery method of a bioprosthetic device in vivo, the methods of the present invention provide greater flexibility than currently available methods, not only with regard to producing tissue swatches for use in bioprosthetic devices, but also with regard to manufacturing bioprosthetic devices.

It is also recognized herein that by reliably permitting the production of tissue swatches according to precise design specifications, the methods of the present invention can reduce the production of unusable tissue swatches, and thus reduce waste and costs currently associated with the manufacture of bioprosthetic devices. Indeed, it has been discovered that the tissue swatches produced according to the methods of the present invention consistently meet desired design specifications, with minimal standard deviations, and thus can increase pericardial tissue valve leaflet yields per pericardial sac.

As contemplated herein, a "tissue sheet" refers to tissue which has yet to be sectioned according to the methods of the present invention.

With regard to bovine pericardial tissue, the native tissue sheets that are typically harvested by slaughter houses have a "rough" side and a "smooth" side, the former being the side of the tissue that was adhered to the heart. While either side of a sheet of native tissue can be subjected to sectioning, typically the rough side of the tissue sheet is subjected to sectioning according to the methods of the present invention. As understood herein, repeated sectioning of the same tissue sheet can be necessary to achieve a tissue swatch of desired uniform or varied thickness.

As contemplated herein, a tissue sheet can be frozen and sectioned using any methods which do not negatively impact the integrity of the tissue swatch for its intended use in a bioprosthetic device. As described herein, methods of freezing a tissue sheet include, but are not limited to, air temperature based convection freezing, metal plate based conduction type freezing, and cryofreezing. As understood herein, for use in the methods of the present invention, tissue sheets are typically frozen at a temperature of from about −5° C. to about −20° C. Typically, when a cryocutting apparatus is used in the methods of the present invention, the temperature of the cryocutting apparatus is adjusted prior to use such the interior chamber is chilled to a temperature of approximately −20° C.

As discussed above, any type of apparatus which permits carefully controlled trimming of tissue sections from a frozen tissue sheet and which can result in a tissue swatch of one or more desired thicknesses can be used in the methods of the present invention. Devices suitable for such trimming are familiar to one of skill in the art and include cryotomes, and may further include microtomes and vibratomes when used under conditions which can maintain the tissue sheet in a frozen state.

It is contemplated herein that a tissue sheet for sectioning is placed on the cutting apparatus (such as a cryotome) and then frozen in place on the cutting apparatus. Similarly, a tissue sheet may be placed on a cold vibratome or microtome (e.g., on a device located in a walk-in freezer) and the tissue sheet subsequently frozen in place on the device. In this regard, it is also contemplated herein that one could introduce a piece of tissue onto a metal plate/puck and the combination (of the tissue on the plate) could be pre-frozen for later use, e.g., in a microtome or a vibratome maintained in a frozen chamber/environment.

Alternatively, the tissue sheet can be frozen according to conventional methods and then placed on the apparatus for sectioning according to the methods of the present invention. Thus, for example, a tissue sheet can be chilled at a temperature between −5° C. to −20° C. and then placed on a cutting apparatus suitable for sectioning tissue (e.g., using embedding medium) as described herein.

As understood by one of skill in the art, the degree to which the tissue sheet is chilled prior to sectioning will depend on the features of the apparatus used for sectioning the tissue sheet; the tissue sheet is frozen such that retention of the tissue sheet on the cutting apparatus, and sectioning of the tissue sheet with the apparatus, is facilitated.

Cryocutting techniques are familiar to one of skill in the art, and refer to conventional methods to produce uniformly thin (micron scale) tissue slices for histological application. Specifically, cryocutting comprises the use of a cryostat microtome, or cryotome, to shave off thin tissue swatches from a larger piece of frozen tissue using a controlled trimming mechanism. The process typically does not negatively impact tissue properties; tissue shavings that are produced for histological applications can be stained, viewed and analyzed under a microscope at a later time point. As envisioned herein, in one embodiment, a tissue sheet suitable for the production of a tissue swatch for incorporation in a bioprosthetic device is placed on the cryotome specimen disk, is frozen on the apparatus, and then sectioned to result in a tissue swatch comprising one or more desired thicknesses.

As discussed, it is also contemplated herein that a tissue sheet can be frozen using conventional methods provided herein prior to being placed on the cryotome. According to the present methods, and in contrast to what is typically the case when a cryotome is used in the field of histology, the pieces of tissue that are removed by sectioning are discarded, and the tissue section remaining on the machine at the end of the procedure is the desired tissue swatch.

As used herein, the term "cryocutting apparatus" and the like refer to a cryotome or other device that can be used to freeze and section tissue swatches as contemplated herein. As discussed above, however, as contemplated herein, pre-frozen tissue sheets can also be sectioned on a cryotome according to the methods of the present invention. As contemplated herein, any commercially available cryotome can be used in the methods of the present invention, and include, for example, commercially available cryostat models such as the Leica CM1850, Leica CM1950, Leica CM1850 UV, Leica CM3050S and the Leica CM1510 S (Leica Microsystems, Buffalo Grove, Ill.). Additional examples of suitable cryotomes include full body dissection cryotomes such as Hacker-Bright model 8250 & 9400 cryostats (Hacker Instruments and Industries, Inc., Winnsboro, S.C.).

One of skill in the art is familiar with the routine operation of tissue cutting apparatuses such as microtomes, vibratomes, and cryocutting apparatuses such as cryotomes, including the procedures necessary to prepare a tissue sheet for sectioning and to adjust the machine prior to (and during) use. These procedures are typically outlined in a manufacturer's instruction manual. For example, with regard to the use of a cryotome, such procedures include, e.g., preparing the specimen disk, including the use of embedding gel and a gel freezing ring to prepare a gel surface on the specimen disk, setting a piece of tissue on a specimen disk, programming the cryocutting apparatus to incorporate the desired sectioning parameters, replacing blades in the cryocutting apparatus, and cutting a piece of tissue with the cryocutting apparatus to produce a tissue swatch comprising one or more regions of desired thickness. See, e.g., FIG. 1.

The size and shape of a tissue sheet for sectioning according to the methods of the present invention can vary depending on the apparatus employed for sectioning. For example, a sheet of tissue of a size suitable for placing on the mounting plate of a cryotome can be removed from a larger tissue sheet, e.g., by using a die punch. The resulting tissue sheets can be, for example, spheres of approximately 55 millimeters in diameter.

Figure 2:
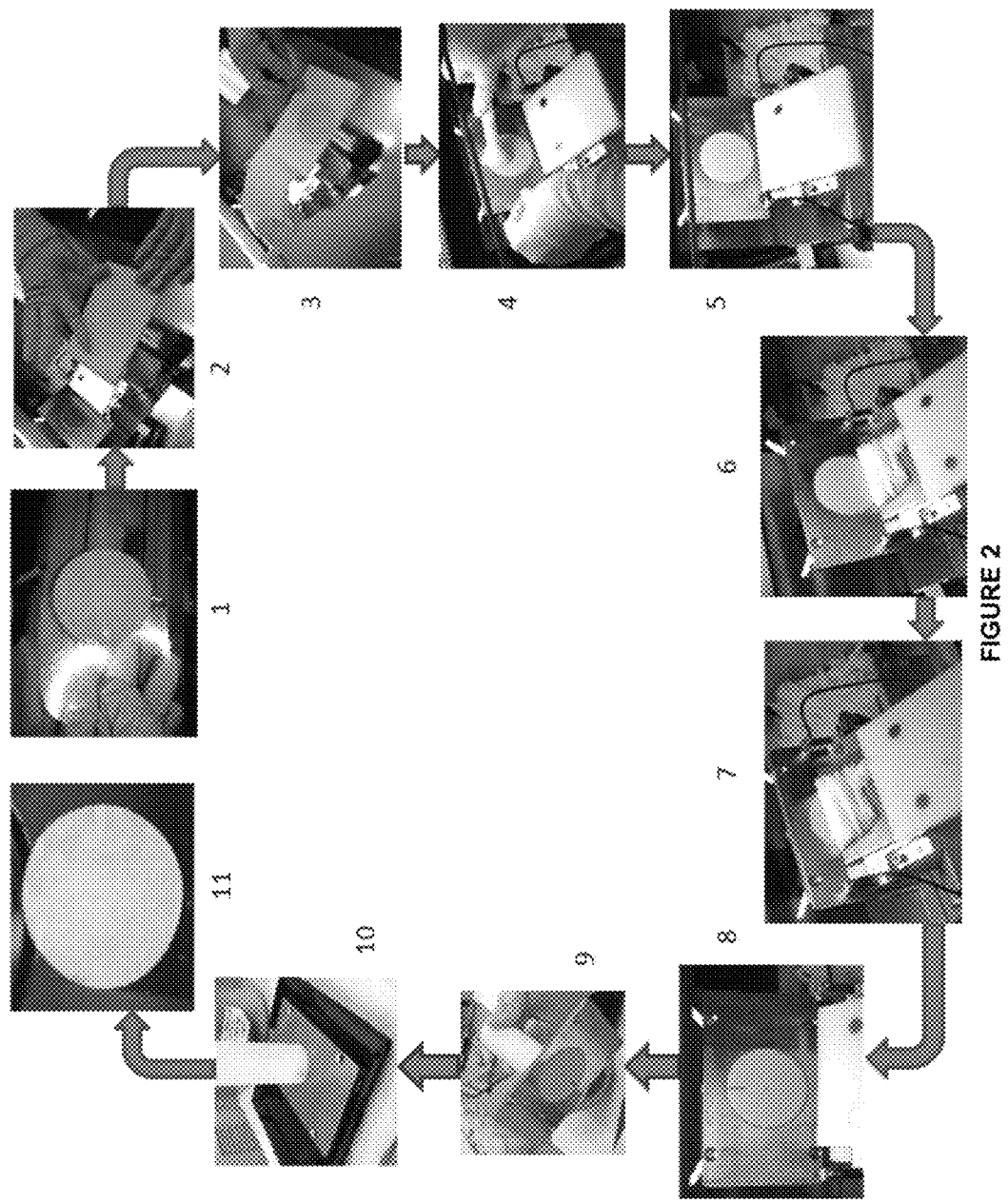
FIG. 2 depicts steps involved in sectioning a tissue sheet on a cryocutting apparatus which does not comprise the use of embedding gel according to a contemplated embodiment of the methods of the present invention. Image 1 depicts introducing a tissue sheet onto a plastic film for easy handling prior to introduction of the tissue sheet into the cryotome. Image 2 depicts dab drying the tissue sheet in order to prevent ice crystals from forming when the tissue is mounted into the cryotome. Image 3 depicts the dried tissue sheet ready to be loaded into the cryotome. Image 4 depicts introducing the tissue sheet into the cryotome and mounting the tissue sheet onto a frozen metal puck using a paint brush to ensure uniform mounting across the entire surface area of the tissue sheet. Image 5 depicts the tissue sheet completely mounted onto the metal puck. Image 6 depicts a snapshot of tissue sheet slicing (at the higher end of the slicing cycle). Image 7 depicts a snapshot of tissue sheet slicing (at the lower end of the slicing cycle). Image 8 depicts a cryocut bovine pericardium tissue swatch prior to removal from the cryotome. Image 9 depicts a cryocut tissue swatch dismounted from the cutting apparatus. Image 10 depicts recovering the cryocut tissue swatch by simple immersion into saline solution at room temperature. Image 11 depicts the cryocut tissue swatch in saline solution at room temperature.

While embedding medium is typically used with cryotomes and other tissue sectioning apparatuses for histological use, as contemplated herein, a tissue sheet of suitable size and shape for sectioning on a cutting apparatus according to the methods of the present invention can be placed directly (without embedding medium) on the specimen disk of the apparatus for sectioning. See, e.g., FIG. 2 which depicts the use of a cryotome in such manner. As contemplated herein, the specimen disk can have a flat surface, or can have been machined to have a contoured surface, in order to produce a tissue swatch of desired varied thickness.

Alternatively, the methods of the present invention can employ a specimen disk which is coated with embedding gel to create a flat surface on which is affixed the piece of tissue for sectioning. For example, a layer of embedding medium approximately ⅛ to ¼ inches thick can be evenly applied to the face of a specimen disk and the disk placed into the chilled chamber (approximately −20° C.) of the cryotome until the medium is frozen. The specimen disk is then introduced into position in the cryotome, and the surface of the frozen embedding medium is conventionally shaved using the cryotome such that a smooth surface (i.e., without bumps, holes and imperfections) is produced for tissue mounting when a flat surface is desired. See, e.g., FIG. 1.

Alternatively, a specimen disk with a contoured surface, either machined or created by coating and contouring the disk with embedding gel ("cryogel"), can serve as a "mold" to produce a tissue swatch with the desired varied thickness when the tissue is cut. With regard to the latter, a contoured gel surface can be prepared, e.g., by texturing embedding gel on the specimen disk of a cutting apparatus such as a cryotome with a shaping plate prior to freezing the gel. As understood herein, a "shaping plate" is any type of mold or other form comprising the necessary contours to create a desired tissue swatch, and can be manufactured for use as provided herein by one of skill in the art using conventional methods. See, e.g., FIGS. 6-9.

Once the gel surface is contoured and frozen, the tissue sheet can be placed on the surface of the contoured frozen gel for sectioning. See, e.g., FIG. 1. It is further contemplated herein that tissue swatches with varying thicknesses can be produced by adjusting the cutting apparatus to employ a specimen disk with a flat surface with or without embedding gel, and cutting the tissue sheet with an apparatus that has been adjusted to incorporate contoured, e.g., convex- or concave-shaped, blades. See, e.g., FIGS. 1 and 2.

Blades for use in the methods of the present invention include, e.g., high and/or low profile steel, gold or diamond blades, and can be obtained from commercial vendors. For example, straight blades can be purchased from Leica Microsystems (Buffalo Grove, Ill.).

Blades for use in the present invention can also be manufactured with different profiles and angles, and such custom blades can be obtained from a variety of commercial vendors. For instance, contoured blades, e.g., blades with concave or convex cutting edges, can be designed and created according to conventional methods by one of skill in the art, e.g., by machining the edge of a commercially available straight blade to achieve the desired contoured blade edge, or otherwise preparing such a blade from suitable materials. See FIGS. 3 and 4.

As contemplated herein, one of skill in the art understands the various physical features necessary for blades for use in a cutting apparatus such as a microtome, vibratome or cryotome. For example, such blades are typically thick enough to provide stability during the cutting process, with a beveled cutting edge parallel to the cutting motion. It is understood herein that custom made contoured blades for use with the methods of the present invention can be designed and manufactured by one of skill in the art in view of such considerations.

Figure 10:
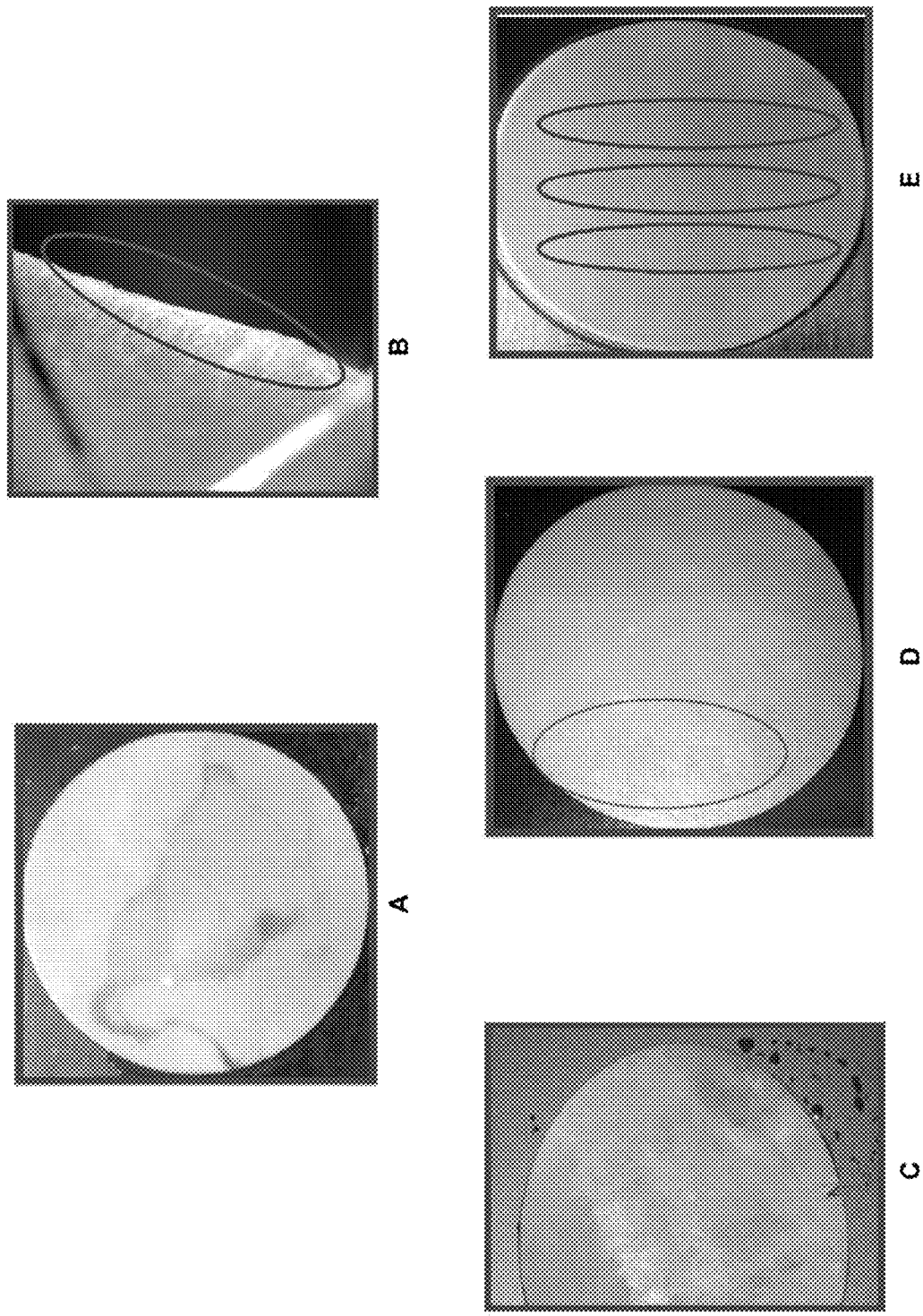
FIG. 10 depicts images of tissue swatches with various physical features (sectioning artifacts) which can render the tissue swatch unacceptable for use in a bioprosthetic device.

In addition, one of skill in the art understands that the blade should be set into a cutting apparatus at an angle that minimizes damaging the specimen and making a tissue swatch with undesirable artifacts, e.g., chatter lines. See FIG. 10. One of skill in the art recognizes that the correct blade angle will ultimately depend on the type of blade (e.g., type of beveled edge), and thus can vary depending on the blade used in the apparatus at any given time.

As used herein, the phrase "wherein said apparatus has been adjusted to produce a tissue swatch of one or more desired thicknesses" encompasses steps required to operate such apparatus familiar to one of skill in the art, including but not limited to, changing out the blade on the cutting apparatus as necessary for routine operation, or as contemplated herein to employ straight or contoured blades to produce a tissue swatch of desired uniform or varied thickness, or to include a specimen disk with a flat or a contoured surface, as desired.

The terms "prostheses" and "prosthetic devices" as used herein are familiar to one of skill in the art and broadly include any artificial device used to replace a missing body part, such as a limb, tooth, eye, or heart valve for extended periods of time. Typical prostheses for cardiovascular application include artificial heart valves, pericardial patches, vascular grafts or conduits, permanently in-dwelling percutaneous devices, vascular shunts, dermal grafts for wound healing, and surgical patches.

As used herein, a "bioprosthetic device" or "bioprosthesis" refers to prosthetic devices which are comprised of one or more natural material components in combination with one or more other natural or synthetic materials. Bioprosthetic devices for cardiovascular use are familiar to one of skill in the art. Examples of such devices include tissue-based heart valve prostheses for transcatheter aortic valve implantation (TAVI). Tissue-based heart valve prostheses can be stentless, in which a tissue heart valve is implanted utilizing the recipient's native support structure, i.e., the aorta or mitral annulus. They can also be stented, in which case a stent serves as a frame for tissue-based leaflets which are positioned on the stent in an assembly that approximates the shape and function of an actual valve.

As contemplated herein, tissue for use in the methods of the present invention must be of suitable source, age and quality for the manufacture of a medical device, specifically, the manufacture of a bioprosthetic device, and more particularly, for use in a cardiovascular bioprosthetic device. Such source, age and quality criteria are familiar to one of skill in the art. For example, tissue for use in the methods provided herein can include, but is not limited to, pericardial tissue harvested from a variety of mammals. Such mammals include, e.g., cows, horses, pigs, dogs, sheep, seals or kangaroos. The use of tissue of human cadaver origin is also contemplated herein. In a particular embodiment, the methods of the present invention can be used to prepare sections of pericardial tissue of human, bovine, equine, ovine or porcine origin.

With regard to bovine pericardial tissue, tissue from adult animals (i.e., animals of approximately 36 months of age or above) has conventionally been used in the manufacture of bioprosthetic cardiovascular devices, as adult tissue is of greater elasticity, and is thicker and thus more durable, than tissue harvested from younger animals. That said, pericardial tissue of young animals (e.g., approximately months of age) is typically thinner than that of adult animals, and has been used in the manufacture of bioprosthetic cardiovascular devices for transcatheter applications where thinner tissue is preferred. As the methods of the present invention can be used to produce tissue swatches of very thin thickness, it is contemplated herein that these methods now make it possible to consistently and reliably employ adult pericardial tissue in the manufacture of bioprosthetic devices for all kinds of bioprosthetic devices, including cardiovascular bioprosthetic devices designed for minimally invasive procedures.

Conventional methods for harvesting and processing tissue for the creation of bioprosthetic devices can be used prior to sectioning a tissue swatch according to the methods of the present invention. Such harvesting and processing techniques are familiar to one of skill in the art and are described in, for example, U.S. 2011/0238167, the entire disclosure of which is incorporated by reference herein. Typically, fresh pericardial sacs are obtained from slaughterhouses and are cut, flattened, and cleaned of excess fat and other impurities. Areas deemed unusable are trimmed away, and the remaining tissue is typically fixed by immersing the tissue in an aldehyde to cross-link the tissue. After a period of quarantine, the tissue can be further processed, which can involve further cleaning and trimming of rough edges and any additional unusable areas to form a tissue sheet.

The thickness of a bovine pericardial tissue sheet harvested according to conventional methods is typically between 300-700 microns (0.0118-0.0275 inches) thick. It is commonly understood that tissue sheets for use in bioprosthetic devices, including pieces of pericardial tissue, are typically selected based on a specific thickness range and other design considerations familiar to one of skill in the art, e.g., lack of holes, thin spots, or other damage to the integrity of the tissue, which can be determined upon a visual inspection of the tissue sheet. Typically, the thickness of a piece of pericardial tissue, including a tissue swatch produced according to the methods of the present invention, can be measured using any conventional method, e.g., using a contact indicator as described in U.S. 2011/0238167, the entire disclosure of which is incorporated by reference herein. A tissue thickness can also be measured using a routine "drop gauge technique" to measure multiple locations on the surface of the tissue substrate after the cryocutting process is completed ("thickness gauge method").

Alternatively, a "feeler gauge method" can be employed in the methods of the present invention which involves, e.g., manually determining the distance between the specimen disk of the cryocutting apparatus and the blade using a chilled feeler gauge. For example, as understood by one of skill in the art, a 0.025" size feeler gauge is a 0.025" gauge block which is placed next to the tissue swatch during cutting. When the cutting blade rubs against the feeler gauge cutting is stopped since the desired thickness has been achieved.

Alternatively, as contemplated herein, one can produce a tissue swatch of a resulting desired thickness after sectioning by first determining the thickness of the piece of tissue to be sectioned, and then calculating the number of sections (of a known cutting depth) necessary to remove the necessary amount of tissue.

Unless otherwise indicated herein, it is understood that the methods described herein can be used in combination with conventional materials and methods for preparing or processing tissues swatches for use in bioprosthetic devices, and that are routinely employed in the manufacture of a bioprosthetic device.

For example, as contemplated herein, the tissue sheet can be subjected to methods designed to decellularize the tissue, cross-link tissue proteins, and/or reduce calcification of the tissue. The tissue can also be subjected to in vivo or in vitro affiliation of cells to enhance the biocompatibility of the tissue. Such additional methods and/or reagents can be employed prior to or after the tissue is sectioned according to the methods of the present invention, and/or prior to or after manufacture of a bioprosthetic device, as appropriate.

In addition, it is understood herein that reagents or manufacturing techniques for use in the methods of the instant invention can include reagents and techniques typically used in cryocutting tissue for histological applications as long as the reagent or technique is compatible with the ultimate intended clinical use of the cryocut tissue swatch. Thus, for example, as contemplated herein, any suitable embedding medium can be used which does not penetrate the tissue, or can be present only in negligible amounts in the final bioprosthetic device, and thus will not otherwise pose any challenges to device biocompatibility, tissue handling and relevant processing. Such reagents are familiar to one of skill in the art and include, e.g., embedding medium such as OCT™ TISSUE-TEK (Sakura Finetek USA, Inc., Torrance, Calif.) Similarly, after sectioning, the cryocut tissue swatch can be removed from the apparatus and briefly immersed in saline solution at room temperature, e.g., for approximately 10 seconds or less to thaw the section prior to recovering the tissue section from the apparatus.

In addition to the manufacture of tissue swatches for bioprosthetic devices, it is contemplated herein that the methods of the present invention also can be used to section any piece of tissue to produce a tissue swatch of any desired uniform or varied thickness for use in any other medical device or clinical application. For example, cryocutting can also be used to trim the loose fibers from the rough side of a tissue sheet to produce a piece of tissue which is more cosmetically appealing for the manufacture of a bioprosthetic device.

It is also contemplated herein that tissue swatches produced as provided herein can be used in other clinical applications or devices. For example, tissue swatches of uniform or varying thickness can be created according to the disclosed methods for use as tissue grafts for cosmetic or reconstructive surgery.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

Example 1

Bovine Swatch Cryocutting Procedure Using Embedding Gel

The following example provides detailed materials and methods for cryocutting bovine tissue comprising the use of embedding gel. This example describes producing a tissue swatch with a thickness of 0.025 inches.

Equipment/Supplies
Consumable Materials and Supplies
0.9% Saline Solution, Sterile
Tissue-Tek O.C.T. Compound (embedding gel)
Leica 818 High Profile Microtome Blades
70% Isopropanol (IPA)
Lint free wipes
Tools and Fixtures
Cryotome Brush
Leica Specimen Disk, 55 mm
Gel Freezing Ring
Swatch Loading Fixture
Saline thaw container
Clean saline container
Fixed Equipment
Leica CM3050 S Cryostat Process Procedure:

All used blades should be disposed of in the shrapnel disposal and handled in the biohazards waste. At the start of each shift the entire work station, the cryostat and ancillary tooling should be cleaned with IPA or 70/30 alcohol and lint free cloth. The tissue loading sheet should be cleaned and disinfected at the end of the shift and should be stored in the cryo chamber when not in use. All ancillary tooling should be free of visual damage; if damaged do not use. The gel container should be wiped with IPA prior to the start of production.

Machine Controls:

To turn on the cryostat place the switch in the upper lock-in position. Unlock the hand wheel by pushing the lock knob to the right. Turn the chamber light on by pressing the light button. Perform line clearance prior to starting. Note that while working with the cryostat the sliding glass door should be kept closed at all times except for when it is necessary to be open for processing reasons.

Specimen Disk and Gel Preparation:

Specimen disks being used should be clean, dry and at room temperature (not frozen). Place the gel freezing ring on the specimen disk such that it is fully seated. Fill the specimen disk with a thin layer of gel (embedding medium), e.g., by starting in the center and working outwards. Place a layer of gel approximately ⅛" to ¼" thick covering the entire surface of the specimen disk all the way out to the gel freezing ring. Take care to avoid air bubbles in the gel. Place the specimen disk and freezing ring into the chamber and onto the quick freeze shelf in the cryostat. Note that the specimen disk and gel freezing ring can be placed on the quick freeze shelf when empty and be filled with gel while in the chamber. Allow gel to fully freeze. Gel will turn white after it is frozen. This will take 5-10 minutes. After gel is frozen, remove gel freezing ring by pushing the specimen disk upwards out of the ring. Note that to aid in removal of the gel freezing ring, one can warm the outer edge of the gel by grasping the ring in their hand. Place the specimen disk back on the quick freeze shelf. Grasping the specimen disk by the outside rubber ring, place the specimen disk onto the specimen head. The back of the specimen disk should be flush with the specimen head surface. Tighten thumb screw. Rotate the blade guard off of the blade to its open position to the left.

Index the specimen head forward using the "Fast Forward" button. When the blade is near the gel surface stop indexing the specimen disk forward. Set the machine to "Sectioning" mode and 20 micron depth of cut by pressing the "Plus" button until 20 microns is displayed on the screen. Set the "Machine Speed Lever" to 0. Press "Section Mode 2" button to set the machine to continuous mode. Press the "Run Enable and Run Stop" buttons simultaneously to start the machine. Slide the "Machine Speed Lever" to 100%. As the gel is removed revealing a smooth surface, dial down the depth of cut from 20 microns to 10 to 5, and finally to 1 for the final few passes. Note that to ensure that the blade does not damage the gel surface, monitor the cut and reduce the depth of cut if chatter or vibrations are noticed. Monitor the gel shaving build up and remove as necessary with a cold brush, and gently brush gel shavings towards the lower right hand side of the chamber.

When the gel surface is completely smooth, and multiple passes at 1 micron have been completed on this surface, stop the machine by pressing the "Run Stop" button. Press the "Home/Fast Backward" button to return the chuck to the home position. Replace the blade guard. Inspect the gel to ensure that surface is completely free of bumps, holes or other imperfections. Gently brush any remaining gel shavings from smooth surface using the cold brush. Note that if there are imperfections on the gel surface additional gel can be added and the above steps can be repeated to obtain a smooth surface. If the imperfections cannot be corrected, wash the gel off in the sink and start this section over.

Tissue Sheet Preparation:

Remove a tissue sheet from its individually labeled container and place into clean saline solution. Place the sheet loading fixture (a flat plastic surface that is use to keep the tissue sheet flat without wrinkles during transfer onto the metal plate of the gel surface) on a flat surface and ensure that it is clean and dry. Remove the sheet from the saline container. Place the sheet "smooth side up" (bovine pericardium has a smooth surface and a rough surface when it is harvested from the cow. The smooth surface is the one that is adhered to the metal plate or the gel surface and the tissue removal is performed on the rough surface) on the sheet loading fixture. Gently pat the sheet with a lint free wipe. Ensure that there are no bubbles or wrinkles in the sheet. The sheet should lie perfectly flat on the sheet loading fixture and be free of excess moisture. Holding the sheet loading fixture by the left side, align the sheet to the far left of the gel surface, centered vertically. Note that it is important to apply the sheet as far left as possible on the gel surface to allow for zeroing the blade in the next section. Gently press the sheet against the gel and wait a moment to allow sheet to adhere to gel. Gently remove sheet loading fixture being sure not to disrupt the sheet or gel surface. Allow sheet to freeze completely. This will take approximately 1 minute.

Zeroing the Blade and Chuck:

Rotate the blade guard off of the blade to its open position to the left. Set the depth of cut to 0 microns by pressing the "Minus" button until 0 microns is displayed. Then manually rotate the hand wheel multiple times to ensure that specimen head is no longer moving forward. Index the specimen head toward the blade using the "Fast Forward" button. When the sheet is near the blade, stop indexing the specimen head forward. Manually rotate the hand wheel until blade is centered on the specimen disk. Grasp the cold 0.025" feeler gauge by the flat end and gently insert between the blade and the gel surface to the right of the sheet. Take great care to avoid contact with blade. Blade is extremely sharp. Slowly index the chuck forward using the "Slow Forward" button until a light resistance is felt between the feeler gauge and the blade. Note that the specimen head can be moved forward or backward to achieve the correct fit with the feeler gauge. Gently slide the feeler gauge up and down to confirm this light resistance. Carefully remove the feeler gauge by sliding upward ensuring that the gel surface does not get damaged. Ensure that the feeler gauge stays clean and free of debris or frost. Wipe the feeler gauge with a lint free wipe when needed. Manually rotate the hand wheel until the specimen head is above the blade.

Cryocutting Sheet:

Set the depth of cut to 5 microns by pressing the "Plus" button until 5 microns is displayed on the screen. Press the "Arrow Down" button until "dnxxx" is displayed on the screen. (Note that the "dn" may be followed by any number. The "dn" just needs to be displayed to set this function.) Press the "Arrow Up" and "Arrow Down" buttons simultaneously to set the stroke counter. Note that the number of strokes can be pre-programmed into this function, and may be automatically displayed after pressing the "Arrow Up" and "Arrow Down" buttons simultaneously. Display should read "dn0xx", with xx being the number of strokes. Set the "Machine Speed Lever" to 0. Press "Section Mode 2" button to set the machine to continuous mode. Press the "Run Enable and Run Stop" buttons simultaneously to start the machine. Slide the "Machine Speed Lever" to 100%. The machine will automatically stop after the programmed number of strokes has been completed. After the machine has completed the desired number of strokes and has stopped, press the "Home/Fast Backward" button to return the chuck to the home position.

If cut tissue displays rough vertical lines or other rough patches, clean the blade station and replace the blade. Ideally, the blade should be replaced after sectioning five swatches.

Blade Change:

Rotate the handle on the right side of the blade holder counterclockwise to release the blade. One can use the magnet on the back of the Leica cryotome brush to slide the blade from the blade holder. When the blade is free from the blade holder, place the blade in the used blade container on the back of the blade cartridge. The blade holder should be clean and free of frost before installing a new blade. Using the blade cartridge, slide the new blade from the cartridge into the open blade holder. One can use the Leica brush to center the blade in the blade holder. After the blade is in the correct position, rotate the handle on the right side of the blade holder forward (clockwise) to clamp the blade in place. Avoid handling the blades with your fingers. One can use the magnet on the Leica brush and the blade cartridge to handle the blades.

Swatch Removal:

Manually rotate the hand wheel to return the specimen head to the topmost position. Loosen the thumb screw and carefully remove the specimen disk from the machine. Replace the blade guard. The object temperature and length of time the swatch was in the cryo-chamber can be recorded at this time; ideally processing should be performed in twenty minutes or less. Thaw the swatch by submerging into a separate clean container of saline. When the swatch falls from the gel surface, remove the swatch from the thawing saline container, and place in the clean saline container. After cutting, the tissue swatch may be rinsed in 0.9% saline and stored in 0.5% glutaraldehyde. The resulting tissue swatch may be inspected as described in Example 2 below.

Example 2

Bovine Swatch Cryocutting Procedure without Using Embedding Gel

The following example provides detailed materials and methods for cryocutting bovine tissue without the use of embedding gel. This example describes producing a tissue swatch with a thickness of 0.035 inches.

Equipment/Supplies
Consumable Materials and Supplies
Description
0.9% Saline Solution, Sterile
Leica 818 High Profile Microtome Blades
Thermo Scientific HP35 Ultra Microtome Blades
70% Isopropanol
Lint Free Wipes
Surgical Marker
Green Table Drapes
Tools and Fixtures
Description
Biohazard Disposal Bags
Swatch Loading Fixture
Tissue Mounting Tray
Inspection Block
Leica Tissue Platen Assembly
Tissue Removal Handle Assembly
Calibrated Timer
Leica Brush
Small Red Brush
0.035" Feeler Gauge
Sharps Container
Stainless Steel Flat Forceps
Fixed EquipmentDescription
Leica CM3050 S Cryostat (Cryo #1)
Process Procedure
Setup:

The entire work station, the cryostat and tooling should be cleaned with 70% Isopropanol and lint free wipes before use. Visually inspect the sheet loading fixture, platen mount assembly, and all tissue platens for damage. If damage is found, do not use. Verify machine is powered on, chamber temperature is set to −8° C. and reading within −6° C. to −10° C. Verify the object temperature is set to −10° C. and reading within −8° C. to −12° C. Unlock the hand wheel by pushing the lock knob to the right. Display screen will display "Locked" if hand wheel is locked. Turn the chamber light on by pressing the light button. Fill the tissue mounting tray and one jar with saline. Saline should be changed after every tissue batch. While working with the cryostat, the sliding glass door should be closed at all times except for when it is necessary to be open for processing reasons.

Tissue Platen Preparation:

Verify that the platen mount assembly is installed in the specimen head. Visually inspect the hard stops and pins on the platen mount assembly for frost and/or debris. If needed, clean the platen mount assembly with a lint free wipe and 70% Isopropanol. The tissue platens should be stored in the cryochamber at all times when not in use. Place the first tissue platen on the platen mount assembly and press firmly against the hard stops. Lock the tissue platen to the platen mount assembly by gently rotating both clamp handles upward to their locked position. Excessive force should not be used when locking the clamp handles.

Sheet Preparation:

Remove a sheet from its container and place into a saline rinse container. Place the sheet loading fixture on a flat surface and clean with a lint free wipe if needed. Remove the sheet from the saline rinse container and place the sheet smooth side up on the smooth side of the sheet loading fixture. Gently pat the sheet with a lint free wipe, making sure that there are no air bubbles or wrinkles in the sheet. The sheet should lie perfectly flat on the sheet loading fixture and be free of excess moisture. If the wipe becomes saturated with saline, replace with a new lint free wipe. While holding the sheet loading fixture by one edge, align the sheet with the laser marked rings on the tissue platen. Use the brush to gently press the sheet against the stainless steel and wait a moment to allow the sheet to adhere. If the sheet does not adhere to the tissue platen this means the platen is not frozen. Scrap sheet and do not process any tissue until the platen is frozen. Gently remove sheet loading fixture from the sheet. Allow sheet to freeze completely. The sheet should turn a darker shade of yellow when frozen. When the sheet is frozen to the tissue platen, press the start button on the calibrated timer. Ideally, the sheet should be fully processed and thawed in saline before 20 minutes has passed.

Zeroing the Blade:

Remove the blade guard. Set the depth of cut to 0 microns by pressing the "Minus" button until 0 microns is displayed. Manually rotate the hand wheel multiple times to ensure specimen head is no longer moving forward. Index the specimen head toward the blade using the "Fast Forward" button until the sheet is near the blade. Manually rotate the hand wheel until blade is centered on the sheet. Grasp the cold 0.035" feeler gauge by one end and gently insert between the blade and the stainless steel surface to the right of the sheet. Take great care to avoid contact with blade as blade is extremely sharp. Slowly index the specimen head forward using the "Slow Forward" button until a light resistance is felt between the feeler gauge and the blade. The specimen head can be moved forward or backward to achieve the correct fit with the feeler gauge. Gently slide the feeler gauge up and down to confirm this light resistance. Carefully remove the feeler gauge being careful not to damage the sheet. Keep the feeler gauge clean and free of debris or frost. Wipe the feeler gauge with a lint free wipe when needed. Manually rotate hand wheel until the sheet is above the blade.

Cryocutting Sheet:

Set the depth of cut to 8 microns by pressing the "Plus" button until 8 microns is displayed on the screen. Press the "Arrow Down" button until "dnxxx" is displayed on the screen. (The "dn" may be followed by any number.) Press the "Arrow Up" and "Arrow Down" buttons simultaneously to set the stroke counter. The number of cuts is preprogrammed into this function, and will be automatically displayed after pressing the "Arrow Up" and "Arrow Down" buttons simultaneously. Display should read "dn0xx", with xx being the number of strokes from the table below. To change the number of cuts that are pre-programmed press the menu key until the Preset Counter screen is displayed. Then press the "Arrow Up" or "Arrow Down" buttons to select the desired number of cuts. After the desired number of cuts has been selected the entry will automatically save after 5 seconds. The table below may be used as a guide to target specific tissue thicknesses.

TABLE 1

Target Tissue Thickness Guide
Depth of Cut 8 microns (.008 mm)

| Target Tissue Thickness | Number of Cuts |
|---|---|
| .010" | 79 |
| .011" | 76 |
| .012" | 73 |
| .013" | 70 |
| .014" | 67 |

Set the "Machine Speed Lever" to 0. Press "Section Mode 2" to set the machine to continuous mode. Press the "Run Enable and Run Stop" buttons simultaneously to start the machine. Slide the "Machine Speed Lever" to 100%. The machine will automatically stop after the programmed number of cuts has been completed. After the machine has completed its cutting cycle, press the "Home/Fast Backward" button to return the specimen head to the home position. Replace the blade guard. All shavings should be brushed away. Replace blade as needed. If cryocut tissue displays rough/fuzzy vertical lines or other rough/fuzzy patches, the blade holder should be cleaned and the blade replaced. Scrap any tissue with visible vertical lines. Manually rotate the hand wheel to return the specimen head to the topmost position. One can mark the top of the sheet with a small vertical line using a surgical marker. One can mark the center of the sheet with a dot using a surgical marker. Loosen the clamps by rotating the clamp handles down and outward to their unlocked position. Carefully remove the tissue platen by pulling forward until the pins disengage. Avoid contacting the blade or blade guard with the tissue platen or sheet.

Swatch Removal:

The resulting sectioned tissue swatch may be thawed by submerging the tissue platen into room temperature saline. If the swatch has been frozen for more than 20 minutes, the tissue swatch should be discarded. Gently remove the thawed swatch from the tissue platen with flat forceps if necessary. Remove the swatch from the saline container, and place in appropriate storage container. Thoroughly dry the tissue platen with a lint free wipe and refreeze for further use. The tissue platen may be placed at the end of the quick freeze shelf to allow sufficient time for the platen to refreeze prior to reuse.

Swatch Inspection:

Place a swatch on an inspection block with the smooth side in contact with the block. Each swatch should be inspected for the following criteria, as certain imperfections may render the tissue swatch less than ideal for use in a bioprosthetic device (see Table 2). Inspections should be performed with unaided eye at approximately 12-18 inches under normal workspace lighting. See FIG. 10.

TABLE 2

Swatch Inspection Criteria

| Inspection Criteria | Acceptable | Reject |
|---|---|---|
| Dry Tissue | No visual signs of dehydration, including hardening of the tissue and crack formation | Visual signs of dehydration |
| Integrity | Delamination on the cut edge | Tears, holes or indentations inside the area of where a |

TABLE 2-continued

Swatch Inspection Criteria

| Inspection Criteria | Acceptable | Reject |
|---|---|---|
| Creases and Wrinkles | Wrinkles | leaflet can potentially be cut Creases |
| Chatter Marks | No visible ridges or rough surface | Any visible ridges or rough surface |
| Thin Spots | No visible thin spots | Any visible thin spots |
| Blade Witness Marks | No visible vertical lines | Any visible vertical lines |

Blade Change:

Rotate the handle on the right side of the blade holder counterclockwise to release the blade. One can use the magnet on the back of the Leica brush to slide the blade from the blade holder. When the blade is free from the blade holder, place the blade in the used blade container on the back of the blade cartridge, or in the sharps container. The blade holder should be clean and free of frost before installing a new blade. Clean the back of the blade holder with a lint free wipe and 70% Isopropanol if needed. Using the blade cartridge, slide the new blade into the open blade holder. One can use the red brush to center the blade in the blade holder. Avoid contacting the blade with anything in the swatch cutting area. This can damage the blade edge and cause defects in the tissue. After the blade is in the correct position, rotate the handle on the right side of the blade holder forward (clockwise) to clamp the blade in place. Care should be taken to avoid handling the blade directly. The machine should be cleaned after each use.

The invention claimed is:

1. A method of manufacturing a bioprosthetic device, comprising:
   a. producing a tissue swatch comprising more than one desired thickness by sectioning a tissue sheet on a cryocutting apparatus having a contoured blade, wherein said tissue sheet is suitable for use in the manufacture of said bioprosthetic device, and wherein said contoured blade has either an elevated region that produces a depressed thickness of said tissue swatch or a depressed region that produces an elevated thickness of said tissue swatch;
   b. configuring said tissue swatch into a shape suitable for use in said bioprosthetic device; and
   c. incorporating said tissue swatch into said bioprosthetic device.

2. The method of claim 1 wherein said apparatus employs a flat specimen disk.

3. The method of claim 1 wherein said apparatus employs a contoured specimen disk.

4. The method of claim 1 wherein said contoured blade is a convex blade and said tissue swatch is of concave thickness.

5. The method of claim 4 wherein said tissue swatch of concave thickness comprises thicker peripheral regions of about 0.014 inches thick, and a thinner inner central region of about 0.010 inches thick.

6. The method of claim 1 wherein said contoured blade is a concave blade and said tissue swatch is of convex thickness.

7. The method of claim 6 wherein said tissue swatch of convex thickness comprises thinner peripheral regions of about 0.010 inches thick, and a thicker inner central region of about 0.014 inches thick.

8. The method of claim 1 wherein said desired thickness is between 0.001 to 0.050 inches, between 0.006 to 0.043 inches, between 0.010 to 0.014 inches or between 0.011 to 0.013 inches.

9. The method of claim 1 wherein said tissue sheet is pericardial tissue.

10. The method of claim 9 wherein said pericardial tissue is selected from the group consisting of pericardial tissue of human, bovine, equine, ovine and porcine origin.

11. The method of claim 10 wherein said pericardial tissue is of bovine origin.

12. The method of claim 1 wherein the bioprosthetic device is selected from the group consisting of artificial heart valves, pericardial patches, vascular grafts or conduits, permanently in-dwelling percutaneous devices, vascular shunts, dermal grafts for wound healing, and surgical patches.

13. The method of claim 12 wherein said bioprosthetic device is a heart valve.

14. The method of claim 1 wherein the tissue swatch is configured for use as a sewing rim, cuff, or leaflet in said bioprosthetic device.

15. The method of claim 1 wherein the tissue swatch is bovine pericardial tissue, and wherein the tissue swatch is configured for use as a valve leaflet in a heart valve.

16. The method of claim 1 wherein said tissue swatch is configured for use in the bioprosthetic device such that one or more regions of greater thickness in said tissue swatch is incorporated in the bioprosthetic device in areas subjected to high stress in vivo.

17. The tissue swatch produced according to the method of claim 1.

18. The bioprosthetic device manufactured according to the method of claim 1.

19. A method of preparing a tissue swatch comprising more than one desired thickness for use in the manufacture of a bioprosthetic device, said method comprising producing a tissue swatch of said more than one desired thickness by sectioning a sheet of frozen tissue on a cryocutting apparatus having a contoured blade, wherein said contoured blade has either an elevated region that produces a depressed thickness of said tissue swatch or a depressed region that produces an elevated thickness of said tissue swatch.

20. A method of manufacturing a bioprosthetic device, comprising:
   a. producing a tissue swatch of more than one desired thickness by sectioning a sheet of frozen tissue on an apparatus having a contoured blade, wherein said apparatus is suitable for controlled trimming of tissue from said sheet of frozen tissue, and wherein said contoured blade has either an elevated region that produces a depressed thickness of said tissue swatch or a depressed region that produces an elevated thickness of said tissue swatch;
   b. configuring said tissue swatch into a shape suitable for use in said bioprosthetic device; and
   c. incorporating said tissue swatch into said bioprosthetic device.

21. The method of claim 20 wherein said apparatus is a high precision tissue slicing apparatus.

22. The method of claim 21 wherein said apparatus is selected from the group consisting of microtomes, vibratomes and cryotomes.

23. The method of claim 22 wherein said apparatus is a cryotome.

\* \* \* \* \*